United States Patent
Rafferty et al.

[11] Patent Number: 5,736,568
[45] Date of Patent: Apr. 7, 1998

[54] 2-(AMINOALKOXY) PHENYLALKYLAMINES WITH ANTIINFLAMMATORY ACTIVITY

[75] Inventors: Paul Rafferty; Gerald Bernard Tometzki, both of Nottingham, Great Britain

[73] Assignee: Knoll Aktiengesellschaft, Ludwigshafen, Germany

[21] Appl. No.: 687,584

[22] PCT Filed: Feb. 20, 1995

[86] PCT No.: PCT/EP95/00626

§ 371 Date: Nov. 25, 1996

§ 102(e) Date: Nov. 25, 1996

[87] PCT Pub. No.: WO95/23127

PCT Pub. Date: Aug. 31, 1995

[30] Foreign Application Priority Data

Feb. 25, 1994 [GB] United Kingdom ............... 9403639

[51] Int. Cl.⁶ ............... A61K 31/135; A61K 31/445; C07C 217/14; C07C 217/18
[52] U.S. Cl. ............... 514/524; 514/538; 514/620; 514/651; 558/422; 560/45; 564/165; 564/352; 564/353; 564/354
[58] Field of Search ............... 564/165, 352, 564/353, 354; 560/45; 558/422; 514/524, 538, 651, 620

[56] References Cited

U.S. PATENT DOCUMENTS

| | | | |
|---|---|---|---|
| 3,047,628 | 7/1962 | Goldberg et al. | 260/570.7 |
| 4,064,125 | 12/1977 | Krapcho | 260/258 |
| 4,098,789 | 7/1978 | Krapcho et al. | 544/299 |
| 4,122,255 | 10/1978 | Krapcho | 542/421 |
| 4,127,606 | 11/1978 | Krapcho | 260/556 |
| 4,156,079 | 5/1979 | Krapcho | 544/169 |
| 4,199,528 | 4/1980 | Krapcho | 260/501.18 |
| 4,214,081 | 7/1980 | Krapcho | 542/424 |

FOREIGN PATENT DOCUMENTS

| | | |
|---|---|---|
| 2173648 | 10/1973 | France. |
| 1604675 | 12/1981 | United Kingdom. |

OTHER PUBLICATIONS

Hayashi et al., *Chem. Pharm. Bull.*, vol. 20, No. 1, pp. 15–20.
Schenker et al., *Helv. Chem. Acta*, 46, pp. 1696–1704, 1963.
Bonjean et al., *Arzneim-Forsch*, vol. 38, No. 4, pp. 501–507, 1988.
Meltzer et al., *J. Org. Chem.*, vol. 22, pp. 612–617, 1957.

Primary Examiner—Richard L. Raymond
Attorney, Agent, or Firm—Keil & Weinkauf

[57] ABSTRACT

Compounds of the formula I

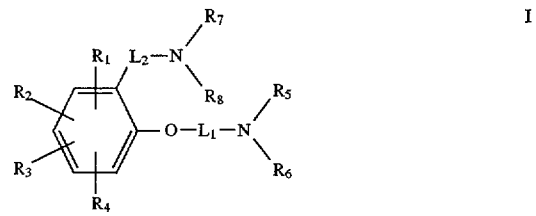

including pharmaceutically acceptable salts thereof are disclosed in which $R_1$, $R_2$, $R_3$, and $R_4$ independently represent hydrogen, hydroxy, halo, halogenated alkyl, halogenated alkoxy, alkyl, alkoxy, cyano, a carbamoyl group, carbonyl group, or $R_1$ and $R_2$ together with the phenyl ring represent a naphthalene ring (optionally substituted); $L_1$ represents $C_{2-6}$ alkylene; $R_5$ represents hydrogen or alkyl, $R_6$ represents hydrogen or alkyl, phenylalkyl (optionally substituted) or $R_5$ and $R_6$ together with the nitrogen atom to which they are attached represent a saturated 3–7 membered heterocyclic ring; $L_2$ represents a $C_{1-6}$ alkylene chain; and $R_7$ and $R_8$ independently represent hydrogen or alkyl or $R_7$ and $R_8$ together with the nitrogen atom to which they are attached represent a saturated 3–7 membered heterocyclic ring. The compounds are anti-inflammatory and/or anti-allergic agents and/or immunomodulants useful in treating rheumatic diseases and/or neurological damage. Compositions containing these compounds and processes to make then are also disclosed.

12 Claims, No Drawings

2-(AMINOALKOXY) PHENYLALKYLAMINES WITH ANTIINFLAMMATORY ACTIVITY

The present application has been filed under 35 U.S.C. § 371 and is based on PCT/EP 95/00626, filed Feb. 20, 1995.

This invention relates to novel substituted 2-(aminoalkoxy)phenylalkylamine compounds having therapeutic activity useful in treating conditions associated with inflammation, allergy, rheumatism, neurological damage or the immune system, to therapeutic compositions containing these novel compounds and to processes for preparing these novel compounds.

It is believed that, in response to an inflammatory stimulus, phospholipase enzymes are activated leading to the release of arachidonic acid from phospholipids. Existing non-steroidal anti-inflammatory agents (NSAIA) are believed to act primarily by blocking the conversion of this released arachidonic acid into prostaglandins via the cyclooxygenase pathway of the arachidonic acid cascade. Many existing NSAIA are unsuitable for use by asthmatics. We have found a series of compounds which act to block the release of arachidonic acid from phospholipids. These compounds are indicated as useful antiinflammatory compounds with a potentially broader spectrum of activity than existing NSAIA, and potentially fewer gastro-intestinal side-effects. In addition the compounds may be useful in the treatment of asthma.

Amides and sulphonamides of formula A

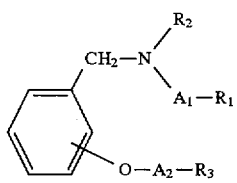

in which $R_1$ is alkyl, cycloalkyl or aryl; $R_2$ is acyl or sulphonyl ; $R_3$ is alkylamino, dialkylamino or a nitrogen containing heterocyclic group; $A_1$ is a saturated bond or an alkylene group having 1 to 4 carbon atoms and $A_2$ is an alkylene group having 2 to 5 carbon atoms, are disclosed as having antiinflammatory activity in U.S. Pat. No. 4,064,125, U.S. Pat. No. 4,127,606 and U.S. Pat. No. 4,122,255. In these documents compounds of formula A in which $R_2$ represents hydrogen are disclosed as chemical intermediates. There is no hint or suggestion that these intermediates have any biological activity.

Compounds of formula B

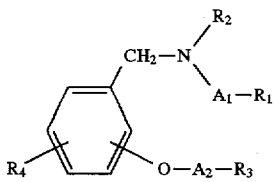

in which $R_1$ is alkyl, cycloalkyl or aryl; $R_2$ is acyl or sulphonyl; $R_3$ is alkylamino, dialkylamino or a nitrogen containing heterocyclic group; $A_1$ is a saturated bond or an alkylene group having 1 to 4 carbon atoms; $A_2$ is an alkylene group having 2 to 5 carbon atoms and $R_4$ is alkoxy, are disclosed as having antiinflammatory activity in U.S. Pat. No. 4,156,079 and U.S. Pat. No. 4,199,528. Compounds of formula B in which $R_2$ represents hydrogen are disclosed as chemical intermediates in these documents. There is no hint or suggestion that these intermediates have any biological activity.

Compounds of formula C

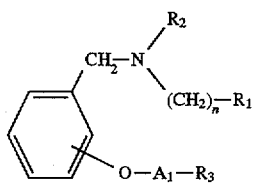

in which $R_1$ is alkoxycarbonyl, amido or substituted amido; $R_2$ is acyl or sulphonyl; $R_3$ is alkylamino, dialkylamino or a nitrogen containing heterocyclic group; $A_1$ is an alkylene group having 2 to 5 carbon atoms and n is 1, 2 or 3, are disclosed as having antiinflammatory activity in U.S. Pat. No. 4,098,789.

Compounds of formula D

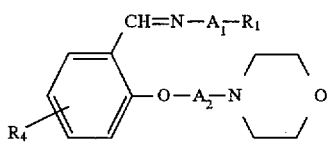

in which $R_1$ is alkyl, cycloalkyl or aryl; $A_1$ is a saturated bond or an alkylene group having 1 to 4 carbon atoms; $A_2$ is an alkylene group having 2 to 5 carbon atoms and $R_4$ is alkoxy are disclosed as useful intermediates in U.S. Pat. No. 4,214,081.

Compounds of formula E

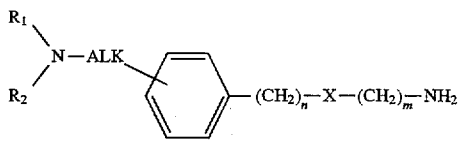

in which $R_1$ and $R_2$ independently represent inter alia hydrogen, lower alkyl, cycloalkyl or aralkyl; X represents inter alia —O—; m is an integer from 2 to 4 inclusive; n is 0, 1 or 2 and ALK denotes a straight or branched alkylene chain of 1 to 6 carbon atoms, are claimed as chemical intermediates in GB 1,604,675. 2(4-Aminobutoxy)-N,N-dimethylbenzenemethanamine is exemplified. There is no suggestion that these compounds possess any pharmacological activity.

Dimethylaminomethyl 2-dimethylaminomethyl-4-methylphenyl ether is disclosed as a chemical intermediate in Chem. Pharm. Bull. 10(1), 15–20 (1972).

N-Isopropyl -2-[2-(isopropylamino)ethoxy]-α-methylbenzylamine and α-methyl-N-propyl-2-[2-(propylamino)ethoxy]benzylamine are disclosed as by-products in Helv. Chim. Acta 46, 1696 (1963).

U.S. Pat. No. 3,047,628 discloses that 2-(dilower alkylamino-lower alkoxy) benzylamines are useful chemical intermediates in the preparation of 2-(dilower alkylamino-lower alkoxy) -N-(3,4,5-trimethoxybenzoyl) benzylamines which are antiemetic agents.

3-[2-Methoxy-6-(1-piperidinylmethyl)phenoxy] propylamine and 3-[2-(1-piperidinylmethyl)phenoxy] propylamine are disclosed as chemical intermediates in Arzneim-Forsch 38(4), 501–7 (1988).

N-[2-(Dialkylaminoethoxy)benzyl]anilines are reported to have antispasmodic effects in Therapie, 12, 558–568 (1957). 1-[(2-Dialkylaminoethoxy)phenyl]-2-amino-1-propanols are disclosed in J. Org. Chem., 22, 612–617 (1957).

The present invention provides novel compounds of formula I

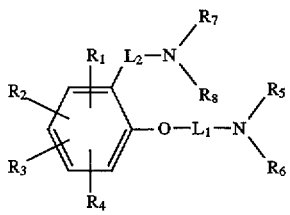

I including pharmaceutically acceptable salts thereof in which $R_1$, $R_2$, $R_3$, and $R_4$ independently represent hydrogen, hydroxy, halo, a halogenated $C_{1-4}$ alkyl group, a halogenated $C_{1-4}$ alkoxy group, a $C_{1-6}$ alkyl group, a $C_{1-6}$ alkoxy group, cyano, a carbamoyl group of formula $CONR_AR_B$ (in which $R_A$ and $R_B$ independently represent hydrogen or a $C_{1-4}$ alkyl group), a ($C_{1-6}$ alkoxy) carbonyl group, or $R_1$ and $R_2$ together with phenyl ring to which they are attached represent a naphthalene ring which is optionally substituted by one or more of the following: a $C_{1-6}$ alkyl group, a $C_{1-6}$ alkoxy group or halo;

$L_1$ represents a $C_{2-6}$ alkylene chain optionally substituted by one or more $C_{1-4}$ alkyl groups;

$R_5$ represents hydrogen or a $C_{1-6}$ alkyl group;

$R_6$ represents hydrogen or a $C_{1-6}$ alkyl group, a phenyl $C_{1-6}$ alkyl chain (in which the alkyl chain is optionally substituted by one or more $C_{1-6}$ alkyl groups and the phenyl ring is optionally substituted by one or more of the following: a $C_{1-6}$ alkyl group, a $C_{1-6}$ alkoxy group, halo, hydroxy, cyano or a carbamoyl group of formula $CONR_cR_d$ in which $R_c$ and $R_d$ independently represent hydrogen or a $C_{1-4}$ alkyl group), or $R_5$ and $R_6$ together with the nitrogen atom to which they are attached represent a saturated 3–7 membered heterocyclic ring, optionally containing sulphur, oxygen or an additional nitrogen atom, wherein the ring is optionally substituted by one or more $C_{1-4}$ alkyl groups;

$L_2$ represents a $C_{1-6}$ alkylene chain optionally substituted by one or more $C_{1-4}$ alkyl groups; and $R_7$ and $R_8$ independently represent hydrogen or a $C_{1-6}$ alkyl group or $R_7$ and $R_8$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups;

excluding the following compounds:

1) 2-(4-aminobutoxy)-N,N-dimethylbenzylamine;
2) N-isopropyl-2-[2-(isopropylamino)ethoxy]-α-methylbenzylamine; and
3) α-methyl-N-propyl-2-[2-(propylamino)ethoxy] benzylamine;

and with the proviso that, when a) $R_1$, $R_2$ and $R_3$ each represent hydrogen and $R_4$ is hydrogen or alkoxy b) $L_1$ represents a $C_{2-6}$ alkylene chain c) the group $NR_5R_6$ is amino, alkylamino, dialkylamino or a nitrogen containing heterocyclic group and d) $L_2$ represents methylene then the group $NR_7R_8$ does not represent amino, alkylamino or piperidino.

It will be understood that a group containing a chain of three or more carbon atoms may be straight or branched, for example propyl includes n-propyl and isopropyl and butyl includes n-butyl, sec-butyl, isobutyl and tert-butyl.

A preferred group of compounds of formula I is represented by formula II

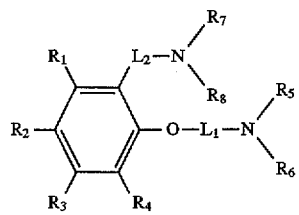

II including pharmaceutically acceptable salts thereof in which $R_1$, $R_2$, $R_3$ and $R_4$ independently represent hydrogen, hydroxy, halo (for example bromo, chloro or fluoro), a polyhalo $C_{1-4}$ alkyl group (for example fluoromethyl, trifluoromethyl or pentafluoroethyl), a $C_{1-6}$ alkyl group (for example methyl, ethyl, propyl, butyl, isobutyl or pentyl), a $C_{1-6}$ alkoxy group (for example methoxy, ethoxy, propoxy, butoxy or pentoxy), cyano, carbamoyl, a ($C_{1-6}$ alkoxy)carbonyl group (for example methoxycarbonyl, ethoxycarbonyl, propoxycarbonyl, butoxycarbonyl or pentoxycarbonyl), or $R_1$ and $R_2$ together with the phenyl ring to which they are attached represent a naphthalene ring;

$L_1$ represents $C_{2-4}$ alkylene chain optionally substituted by one or more $C_{1-4}$ alkyl groups, (for example $L_1$ is methylene, ethylene, trimethylene, propylene or tetramethylene);

$R_5$ represents hydrogen or a $C_{1-6}$ alkyl group (for example methyl, ethyl, propyl, butyl, isobutyl or pentyl);

$R_6$ represents a $C_{1-6}$ alkyl group (for example methyl, ethyl, propyl, butyl, isobutyl or pentyl), a phenyl $C_{1-6}$ alkyl chain [in which the alkyl chain is optionally substituted by one or more $C_{1-6}$ alkyl groups and the phenyl ring is optionally substituted by one or more of the following: a $C_{1-6}$ alkyl group, a $C_{1-6}$ alkoxy group, halo, hydroxy, cyano or carbamoyl; (for example $R_6$ is benzyl, phenylethyl, α,α-dimethylbenzyl or phenylpropyl)] or $R_5$ and $R_6$ together with the nitrogen atom to which they are attached represent a pyrrolidine ring, a piperidine ring, a morpholine ring, a thiamorpholine ring, an azepine ring or an N-methylpiperazine ring;

$L_2$ represents a $C_{1-4}$ alkylene chain optionally substituted by one or more $C_{1-4}$ alkyl groups (for example $L_2$ is methylene, ethylene, trimethylene, propylene or tetramethylene); and $R_7$ and $R_8$ independently represent hydrogen or a $C_{1-6}$ alkyl group, (for example methyl, ethyl, propyl, butyl, isobutyl or pentyl) or $R_7$ and $R_8$ together with the nitrogen atom to which they are attached represent a pyrrolidine ring, a piperidine ring, a morpholine ring, a thiamorpholine ring, an azepine ring or an N-methylpiperazine ring.

In a more preferred group of compounds of formula II $R_1$ represents hydrogen, halo or cyano;

$R_2$ represents hydrogen, halo, a perfluoro$C_{1-4}$alkyl group, hydroxy, cyano, carbamoyl, a $C_{1-4}$ alkoxy group or a ($C_{1-4}$ alkoxy)carbonyl group;

or $R_1$ and $R_2$ together with the phenyl ring to which they are attached represent a naphthalene ring;

$R_3$ represents hydrogen, halo or a $C_{1-4}$ alkoxy group;

$R_4$ represents hydrogen or halo;

$L_1$ represents a $C_{2-4}$ alkylene chain optionally substituted by one or more $C_{1-4}$ alkyl groups;

$L_2$ represents a $C_{1-3}$ alkylene chain optionally substituted by one or more $C_{1-4}$ alkyl groups;

$R_5$ represents hydrogen or a $C_{1-4}$ alkyl group;

$R_6$ represents a $C_{1-4}$ alkyl group, or a phenyl $C_{1-4}$ alkyl chain in which the phenyl ring is optionally substituted by one or more of the following: halo, hydroxy, cyano or carbamoyl;

or $R_5$ and $R_6$ together with the nitrogen atom to which they are attached represent a piperidine ring;

$R_7$ and $R_8$ independently represent hydrogen or a $C_{1-4}$ alkyl group;

or $R_7$ and $R_8$ together with the nitrogen atom to which they are attached represent a piperidine ring.

Preferred values of the substituents in formula II will now be given.

Preferably $R_1$ represents hydrogen, chloro or cyano or $R_1$ and $R_2$ together with the phenyl ring to which they are attached represent a naphthalene ring. More preferably $R_1$ represents hydrogen or chloro or $R_1$ and $R_2$ together with the phenyl ring to which they are attached represent a naphthalene ring. Most preferably $R_1$ represents hydrogen or chloro.

Preferably $R_2$ represents hydrogen, chloro, fluoro, methoxy, trifluoromethyl, hydroxy, cyano, carbamoyl or methoxycarbonyl. More preferably $R_2$ represents hydrogen, fluoro or chloro. Most preferably $R_2$ represents hydrogen or chloro.

Preferably $R_3$ represents hydrogen, chloro or methoxy. More preferably $R_3$ represents hydrogen or chloro. Most preferably $R_3$ represents hydrogen.

Preferably $R_4$ represents hydrogen or chloro. More preferably $R_4$ represents hydrogen.

Preferably $L_1$ represents ethylene or trimethylene. More preferably $L_1$ represents ethylene.

Preferably $L_2$ represents methylene.

Preferably $R_5$ represents hydrogen or methyl or $R_5$ and $R_6$ together with the nitrogen atom to which they are attached represent a piperidine ring. More preferably $R_5$ represents hydrogen or methyl. Most preferably $R_5$ represents methyl.

Preferably $R_6$ represents benzyl, 4-cyanobenzyl, 4-carbamoylbenzyl, 4-chlorobenzyl, 1-(4-chlorophenyl)-1-methylethyl, 2-hydroxybenzyl, 2-chlorobenzyl or methyl. More preferably $R_6$ represents benzyl, 4-chlorobenzyl, 1-(4-chlorophenyl)-1-methylethyl, 2-hydroxybenzyl, 2-chlorobenzyl or methyl. Most preferably $R_6$ represents benzyl, 4-chlorobenzyl, 2-hydroxybenzyl, 2-chlorobenzyl, or 1-(4-chlorophenyl)-1-methylethyl.

Preferably $R_7$ represents hydrogen or methyl or $R_7$ and $R_8$ together with the nitrogen atom to which they are attached represent a piperidine ring. More preferably $R_7$ represents methyl.

Preferably $R_8$ represents hydrogen or methyl. More preferably $R_8$ represents methyl.

In a most preferred group of compounds of formula II, one of $R_1$, $R_2$, $R_3$ and $R_4$ represents halo and the others represent hydrogen; $L_1$ represents ethylene or trimethylene; $R_5$ represents methyl; $R_6$ represents benzyl (optionally substituted by halo or hydroxy); $L_2$ represents methylene; and $R_7$ and $R_8$ both represent methyl.

Specific compounds of formula I are:

2-[2-(N-benzyl-N-methylamino)ethoxy]-6-chloro-N,N-dimethylbenzylamine

2-[2-(N-benzyl-N-methylamino)ethoxy]-3-chloro-N,N-dimethylbenzylamine

2-[2-(N-benzyl-N-methylamino)ethoxy]-5-fluoro-N,N-dimethylbenzylamine

4-[2-(N-benzyl-N-methylamino)ethoxy]-3-(dimethylaminomethyl)benzonitrile

2-[2-(N-benzyl-N-methylamino)ethoxy]-4,5-dichloro-N,N-dimethylbenzylamine

2-[2-(N-benzyl-N-methylamino)ethoxy]-4-chloro-N,N-dimethylbenzylamine

2-[2-(N-benzyl-N-methylamino)ethoxy]-N,N-dimethyl-5-trifluoromethylbenzylamine

N-benzyl-2-[1-(dimethylaminomethyl)naphth-2-yloxy]-N-methylethylamine

2-[2-(benzylamino)ethoxy]-5-chloro-N,N-dimethylbenzylamine

4-{N-[2-(4-chloro-2-dimethylaminomethylphenoxy)ethyl]-N-[methyl]aminomethyl}benzonitrile N-benzyl-2-[4-chloro-2-(piperidinomethyl)phenoxy]-N-methylethylamine 2-[3-(N-benzyl-N-methylamino)propoxy]-5-chloro-N,N-dimethylbenzylamine 2-[2-(N-benzyl-N-methylamino)ethoxy]-5,6-dichloro-N,N-dimethylbenzylamine 2-{2-[N-(2-chlorobenzyl)-N-methylamino]ethoxy}-N,N-dimethylbenzylamine 3-[2-(N-benzyl-N-methylamino)ethoxy]-2-(dimethylaminoethyl)benzonitrile 5-chloro-2-(2-piperidinoethoxy)-N,N-dimethylbenzylamine 2-{2-[N-(4-chlorobenzyl)-N-methylamino]ethoxy}-N,N-dimethylbenzylamine 2-[2-(N-benzyl-N-methylamino)ethoxy]-4-methoxy-N,N-dimethylbenzylamine 2-(2-diethylaminoethoxy)-N,N-dimethylbenzylamine 2-[2-(N-benzyl-N-methylamino)ethoxy]-N,N-dimethylbenzylamine 2-[2-(N-benzyl-N-methylamino)ethoxy]-5-chloro-N,N-dimethylbenzylamine 5-chloro-2-(2-dimethylaminoethoxy)-N,N-dimethylbenzylamine 2-(2-dimethylaminoethoxy)-N,N-dimethylbenzylamine dihydrochloride N,N-dimethyl-2-(3-dimethylaminopropoxy)benzylamine 5-chloro-2-(2-dimethylaminoethoxy)-N,N-dimethylbenzylamine methyl 4-[2-(N-benzyl-N-methylamino)ethoxy]-3-(dimethylaminomethyl)benzoate 2-[2-(N-benzyl-N-methylamino)ethoxy]-5-methoxybenzylamine 2-[2-(N-benzyl-N-methylamino)ethoxy]-5-chlorobenzylamine 2-[3-(N-benzyl-N-methylamino)propoxy]-6-chlorobenzylamine 4-{N-[2-(4-chloro-2-dimethylaminomethylphenoxy)ethyl]-N-[methyl]aminomethyl}benzamide 4-{2-[N-(4-chlorobenzyl)-N-methylamino]ethoxy}-3-(dimethylaminomethyl)benzamide 4-[2-(N-benzyl-N-methylamino)ethoxy]-3-(dimethylaminomethyl)phenol 2-{N-[2-(3-chloro-2-dimethylaminomethylphenoxy)ethyl]-N-[methyl]aminomethyl}phenol 2-[2-(N-benzyl-N-methylamino)ethoxy]-5-methoxy-N,N-dimethylbenzylamine 2-[3-(N-benzyl-N-methylamino)propoxy]-6-chloro-N,N-dimethylbenzylamine 2-[2-(4-chloro-α,α-dimethylbenzylamino)ethoxy]-N,N-dimethylbenzylamine 2-[2-(N-benzyl-N-methylamino)ethoxy]-6-chlorobenzylamine including pharmaceutically acceptable salts thereof, in the form of individual enantiomers, racemates or other mixtures of enantiomers.

The compounds of formula I may form organic or inorganic salts, for example, the compounds of formula I may form acid addition salts with inorganic or organic acids, e.g. hydrochloric acid, hydrobromic acid, fumaric acid, tartaric acid, citric acid, sulphuric acid, hydriodic acid, phosphoric acid, maleic acid, acetic acid, succinic acid, benzoic acid, pamoic acid, palmitic acid, dodecanoic acid and acidic amino acids such as glutamic acid. Some compounds of formula I may form base addition salts, for example, with alkali metal hydroxides for example sodium hydroxide, or with aminoacids for example, lysine or arginine. It will be appreciated that such salts, provided they are pharmaceutically acceptable may be used in therapy in place of the corresponding compounds of formula I. Such salts are prepared by reacting the compound of formula I with a suitable acid or base in a conventional manner. Such salts may also exist in the form of solvates (for example, hydrates).

Certain compounds of formula I may exist in zwitterionic form, for example when $R_1$, $R_2$, $R_3$ or $R_4$ represents hydroxy. Such forms are included within the scope of the present invention.

It will be appreciated by those skilled in the art that certain compounds of formula I contain one or more chiral centers. Certain of the substituents $R_1$–$R_8$ may also contain at least one chiral centre, for example when one of $R_1$–$R_8$ is sec-butyl.

When a compound of formula I contains a single chiral centre it may exist in two enantiomeric forms. The present invention includes individual enantiomers and mixtures of those enantiomers. The enantiomers may be obtained by methods known to those skilled in the art. Such methods typically include resolution via formation of diastereoisomeric salts or complexes which may be separated, for example, by crystallisation; resolution via formation of diastereoisomeric derivatives or complexes which may be separated, for example, by crystallisation, gas-liquid or liquid chromatography; selective reaction of one enantiomer by reaction with an enantiomer-specific reagent, for example, enzymatic esterification, oxidation or reduction, followed by separation of the modified and unmodified enantiomers; or gas-liquid or liquid chromatography in a chiral environment, for example on a chiral support such as silica with a bound chiral ligand or in the presence of a chiral solvent. It will be appreciated that where the desired enantiomer is converted into another chemical entity by one of the separation processes described above, a further step will subsequently be required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of formula I contains more than one chiral centre it may exist in diastereoisomeric forms. The diastereoisomeric pairs may be separated by methods known to those skilled in the art, for example, chromatography or crystallisation and the individual enantiomers within each pair may be separated as described above. The present invention includes each diastereoisomer of compounds of formula I or II and mixtures thereof.

Certain compounds of formula I may exist in more than one crystal form and the present invention includes each crystal form and mixtures thereof. Certain compounds of formula I may also exist in the form of solvates, for example hydrates, and the present invention includes each solvate and mixtures thereof.

The present invention also provides pharmaceutical compositions comprising a therapeutically effective amount of a compound of formula I

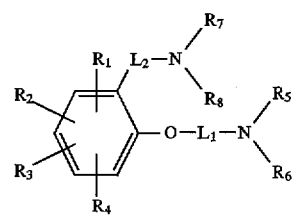

including pharmaceutically acceptable salts thereof in which $R_1$, $R_2$, $R_3$, and $R_4$ independently represent hydrogen, hydroxy, halo, a halogenated $C_{1-4}$ alkyl group, a halogenated $C_{1-4}$ alkoxy group, a $C_{1-6}$ alkyl group, a $C_{1-6}$ alkoxy group, cyano, a carbamoyl group of formula $CONR_AR_B$ (in which $R_A$ and $R_B$ independently represent hydrogen or a $C_{1-4}$ alkyl group), a ($C_{1-6}$ alkoxy) carbonyl group, or $R_1$ and $R_2$ together with the phenyl ring to which they are attached represent a naphthalene ring which is optionally substituted by one or more of the following: a $C_{1-6}$ alkyl group, a $C_{1-6}$ alkoxy group or halo;

$L_1$ represents a $C_{2-6}$ alkylene chain optionally substituted by one or more $C_{1-4}$ alkyl groups;

$R_5$ represents hydrogen or a $C_{1-6}$ alkyl group;

$R_6$ represents hydrogen or a $C_{1-6}$ alkyl group, a phenyl $C_{1-6}$ alkyl chain (in which the alkyl chain is optionally substituted by one or more $C_{1-6}$ alkyl groups and the phenyl ring is optionally substituted by one or more of the following: a $C_{1-6}$ alkyl group, a $C_{1-6}$ alkoxy group, halo, hydroxy, cyano or a carbamoyl group of formula $CONR_cR_d$ in which $R_c$ and $R_d$ independently represent hydrogen or a $C_{1-4}$ alkyl group), or $R_5$ and $R_6$ together with the nitrogen atom to which they are attached represent a saturated 3–7 membered heterocyclic ring, optionally containing sulphur, oxygen or an additional nitrogen atom, wherein the ring is optionally substituted by one or more $C_{1-4}$ alkyl groups;

$L_2$ represents a $C_{1-6}$ alkylene chain optionally substituted by one or more $C_{1-4}$ alkyl groups; and $R_7$ and $R_8$ independently represent hydrogen or a $C_{1-6}$ alkyl group or $R_7$ and $R_8$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups;

together with a pharmaceutically acceptable diluent or carrier. Such pharmaceutical compositions may be used in the treatment of inflammatory and/or allergic diseases and/or diseases with an immunological association and/or rheumatic diseases and/or conditions in which there is neurological damage.

As used hereinafter, the term "active compound" denotes a compound of formula I or a pharmaceutically acceptable salt thereof. In therapeutic use the active compound may be administered orally, rectally, parenterally, topically, ocularly, aurally, nasally, intravaginally or to the buccal cavity, to give a local and/or a systemic effect. Thus the therapeutic compositions of the present invention may take the form of any of the known pharmaceutical compositions for such methods of administration. The compositions may be formulated in a manner known to those skilled in the art so as to give a controlled release, for example rapid release or sustained release, of the compounds of the present invention. Pharmaceutically acceptable carriers suitable for use in such compositions are well known in the art of pharmacy. The compositions of the invention suitably contain 0.1–90% by weight of active compound. The compositions of the invention are generally prepared in unit dosage form.

Compositions for oral administration are the preferred compositions of the invention and these are the known pharmaceutical forms for such administration, for example tablets, capsules, granules, syrups and aqueous or oily suspensions. The excipients used in the preparation of these compositions are the excipients known in the pharmacists' art.

Tablets may be prepared from a mixture of the active compound with fillers, for example, lactose or calcium phosphate, disintegrating agents, for example maize starch, lubricating agents, for example magnesium stearate, binders for example microcrystalline cellulose or polyvinyl pyrrolidone and other optional ingredients known in the art to permit tableting the mixture by known methods. The tablets may, if desired, be coated using known methods and excipients which may include enteric coating using for example hydroxypropylmethylcellulose phthalate.

The tablets may be formulated in a manner known to those skilled in the art so as to give a sustained release of the compounds of the present invention. Such tablets may if desired be provided with enteric coatings by known methods, for example by the use of cellulose acetate phthalate.

Similarly capsules, for example hard or soft gelatin capsules containing the active compound with or without added excipients, may be prepared by known methods and, if desired, provided with enteric coatings in a known manner. The contents of the capsule may be formulated using known methods to give sustained release of the active compound. Enteric coated compositions of the invention may be advantageous, depending on the nature of the active compound. The tablets and capsules may conveniently each contain 1–1000 mg (for example 10 mg, 50 mg, 100 mg, 200 mg, 400 mg, 600 mg or 800 mg) of the active compound. Other compositions for oral administration include, for example, aqueous suspensions containing the compound of formula I in an aqueous medium in the presence of a non-toxic suspending agent such as sodium carboxymethylcellulose, and oily suspensions containing a compound of the present invention in a suitable vegetable oil, for example sunflower oil.

The active compound may be formulated into granules with or without additional excipients. The granules may be ingested directly by the patient or they may be added to a suitable liquid carrier (for example water) before ingestion. The granules may contain disintegrants (for example a pharmaceutically acceptable effervescent couple formed from an acid and a carbonate or bicarbonate salt) to facilitate dispersion in the liquid medium.

Compositions of the invention suitable for rectal administration are the known pharmaceutical forms for such administration, for example suppositories with hard fat, semi-synthetic glycerides or polyethylene glycol bases.

Compositions of the invention suitable for parenteral administration are the known pharmaceutical forms for such administration, for example sterile suspensions in aqueous and oily media or sterile solutions in a suitable solvent.

Compositions for topical administration may comprise a matrix in which the active compound is dispersed so that it is held in contact with the skin in order to administer the compound of formula I transdermally. Alternatively the active compound may be dispersed in a cream, gel or ointment base or applied in the form of a spray.

Compositions of the invention suitable for inhalation via the mouth and/or the nose are the known pharmaceutical forms for such administration, for example aerosols, nebulised solutions or powders. Metered dose systems, known to those skilled in the art, may be used.

Compositions suitable for application to the buccal cavity include slow dissolving tablets, troches, chewing gum, gels, pastes, powders, mouthwashes or rinses.

The compounds of the present invention may also be administered by continuous infusion either from an external source, for example by intravenous infusion or from a source of the compound placed within the body. Internal sources include implanted reservoirs containing the compound to be infused which is continuously released for example by osmosis and implants which may be a) liquid such as an oily solution or suspension of the compound to be infused for example in the form of a very sparingly water-soluble derivative such as a dodecanoate salt or b) solid in the form of an implanted support for example a synthetic resin or waxy material for the compound to be infused. The support may be a single body containing all the compound or a series of several bodies each containing part of the compound to be delivered.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients, for example: a) an analgesic, for example codeine or paracetamol, or a non-steroidal anti-inflammatory agent for example ibuprofen or flurbiprofen (including the R and S enantiomers of each) (e.g. in treatment of rheumatoid arthritis), b) a bronchodilator, for example a $\beta 2$ agonist, or a phosphodiesterase inhibitor, for example theophylline (e.g. in treatment of asthma), c) a non-sedating antihistamine (e.g. in treatment of other allergic conditions) or d) a steroid.

The pharmaceutical compositions containing a therapeutically effective amount of a compound of formula I may be used to treat inflammatory and/or allergic conditions in human beings. In such treatment the amount of the compound of formula I administered per day is in the range 0.1 to 3000 mg. Specific compounds which may be incorporated into the compositions of this invention are the novel compounds disclosed above.

The therapeutic activity of compounds of formula I has been demonstrated by means of tests on standard laboratory animals. Such tests include, for example, the oral administration of the compounds to rats in which an inflammatory condition is induced. Thus, compounds of formula I are useful for the treatment of inflammatory conditions in mammals. Whilst the precise amount of active compound administered will depend on a number of factors, for example the age of the patient, the severity of the condition and the past medical history and always lies within the sound discretion of the administering physician, a suitable dose for enteral administration to mammals, including humans, is generally within the range 0.01–80 mg/kg/day, more usually 0.2–40 mg/kg/day given in single or divided doses. For parenteral administration, a suitable dose is generally within the range 0.01–80 mg/kg/day, more usually 0.2–40 mg/kg/day given in single or divided doses or by continuous infusion. Oral administration is preferred.

Compounds of formula I

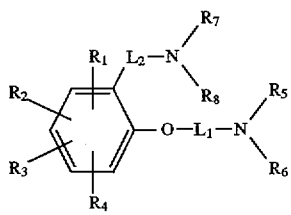

including pharmaceutically acceptable salts thereof in which $R_1$, $R_2$, $R_3$, and $R_4$ independently represent hydrogen, hydroxy, halo, a halogenated $C_{1-4}$ alkyl group, a halogenated $C_{1-4}$ alkoxy group, a $C_{1-6}$ alkyl group, a $C_{1-6}$ alkoxy group, cyano, a carbamoyl group of formula $CONR_AR_B$ (in which $R_A$ and $R_B$ independently represent hydrogen or a $C_{1-4}$ alkyl group), a ($C_{1-6}$ alkoxy) carbonyl group, or $R_1$ and $R_2$ together with phenyl ring to which they are attached represent a naphthalene ring which is optionally substituted by one or more of the following: a $C_{1-6}$ alkyl group, a $C_{1-6}$ alkoxy group or halo;

$L_1$ represents a $C_{2-6}$ alkylene chain optionally substituted by one or more $C_{1-4}$ alkyl groups;

$R_5$ represents hydrogen or a $C_{1-6}$ alkyl group;

$R_6$ represents hydrogen or a $C_{1-6}$ alkyl group, a phenyl $C_{1-6}$ alkyl chain (in which the alkyl chain is optionally substituted by one or more $C_{1-6}$ alkyl groups and the phenyl ring is optionally substituted by one or more of the following: a $C_{1-6}$ alkyl group, a $C_{1-6}$ alkoxy group, halo, hydroxy, cyano or a carbamoyl group of formula $CONR_cR_d$ in which $R_c$ and $R_d$ independently represent hydrogen or a $C_{1-4}$ alkyl group), or $R_5$ and $R_6$ together with the nitrogen atom to which they are attached represent a saturated 3–7 membered heterocyclic ring, optionally containing sulphur, oxygen or an additional nitrogen atom, wherein the ring is optionally substituted by one or more $C_{1-4}$ alkyl groups;

$L_2$ represents a $C_{1-6}$ alkylene chain optionally substituted by one or more $C_{1-4}$ alkyl groups; and $R_7$ and $R_8$ independently represent hydrogen or a $C_{1-6}$ alkyl group or $R_7$ and $R_8$ together with the nitrogen atom to which they are attached represent a saturated 3–7 membered heterocyclic ring, optionally containing sulphur, oxygen or an additional nitrogen atom, wherein the ring may be optionally substituted by one or more $C_{1-4}$ alkyl groups; are indicated for use as medicaments.

Compounds of formula I and pharmaceutically acceptable salts thereof (including the three excluded compounds and the compounds in the proviso) are useful in the treatment (including therapy and prophylaxis) of inflammatory and/or allergic conditions for example musculoskeletal disorders for example: rheumatoid arthritis, osteo-arthritis, systemic lupus erythematosus, muscle trauma, gout, ankylosing spondylitis, tendonitis and bursitis; respiratory disorders for example: asthma and rhinitis; gastrointestinal disorders for example: gastritis, Crohn's disease, ulcerative colitis and other inflammatory diseases of the bowel; diseases of the oral cavity for example: periodontitis, gingivitis and alveolar bone resorption; cutaneous disorders for example: psoriasis, urticaria, allergic skin diseases, burns, ocular inflammation and iritis. Compounds of formula I and salts thereof may also be useful as analgesics and/or anti-pyretic agents.

Accordingly, in another aspect, the present invention also includes a method of treating conditions associated with inflammation and/or allergy comprising the administration of a therapeutically or prophylactically effective amount of a compound of formula I including pharmaceutically acceptable salts thereof (including the three excluded compounds and the compounds in the proviso) to a mammal in need thereof.

While the precise mechanism of action of the compounds of formula I is unknown at present, it is believed that the pharmacological effects arise from the ability of these compounds to inhibit the release of arachidonic acid from phospholipids. Consequently, in a preferred aspect, the present invention provides a method of treating inflammatory and/or allergic conditions comprising the administration of a therapeutically or prophylactically effective amount of an arachidonic acid release inhibitor of formula I (including the three excluded compounds and the compounds in the proviso) to a mammal in need thereof.

The compounds of formula I may also be indicated for use as immunomodulatory agents, generally as immunosuppressants, but some compounds, in certain disease states, may exhibit immunostimulant activity. The compounds according to the invention may be useful in the treatment of diseases resulting from an aberrant immune reaction. Thus the pharmaceutical compositions containing a therapeutically effective amount of a compound of formula I including pharmaceutically acceptable salts thereof (including the three excluded compounds and the compounds of the proviso) may be used to treat diseases with an immunological association for example tissue rejection, such as kidney rejection; autoimmune diseases, such as thyroiditis and type 1 diabetes; cutaneous disorders, such as contact sensitivity and eczema; neoplasia, such as melanoma; and HIV infection.

In such treatment the amount of the compound of formula I administered per day will be such as to give a therapeutic effect and is generally in the range 0.1 to 2000 mg. preferably 1 to 500 mg.

Accordingly, in another aspect, the present invention also includes a method of treating conditions associated with the immune system, comprising the administration of a therapeutically or prophylactically effective amount of a compound of formula I including pharmaceutically acceptable salts thereof (including the three excluded compounds and the compounds of the proviso) to a mammal in need thereof.

The therapeutic activity of compounds falling within formula I may be demonstrated by means of in vitro and in vivo tests. Such tests include, for example, the in vitro mixed lymphocyte reaction and an in vivo rat Graft versus Host (GvH) test. Thus, compounds of formula I may be useful as immunomodulatory agents.

The compounds according to the present invention may be useful in the treatment of neurological damage. The term "neurological damage" as used in this specification includes inter alia brain trauma, cerebral ischaemia, haemorrhage, head injuries, stroke and neurodegenerative diseases including Dementia, Alzheimer's Disease, Parkinson's Disease, Huntington's Chorea, Pick's Disease, Post Traumatic Dementia and Creutzfeldt-Jakob's Disease. Such activity may be demonstrated by tests on standard laboratory animals which include techniques such as transvascular occlusion of the middle cerebral artery in rats and the rat bilateral carotid occlusion global model. The activity may also be demonstrated by the inhibition of superoxide production in purified mouse microglial cells which have been exposed to aluminosilicate as described by Evans et al in Free Radicals and Aging, pages 178–189, edited by I. Emerit & B. Chance, published by Birkhauser Verlag, 1992, and references cited therein. Alternatively such activity may be demonstrated by preventing impairment of the acquisition and retention of memory as a result of electroconvulsive shock treatment to rats (Leher, B. et al., 1986, Physiology & Behaviour, 36, 471–475).

Accordingly, in another aspect, the present invention provides a method of treating neurological damage comprising the administration of a therapeutically or prophylactically effective amount of a compound of formula I including pharmaceutically acceptable salts thereof (including the three excluded compounds and the compounds in the proviso) to a mammal in need thereof.

The compounds of formula I including pharmaceutically acceptable salts thereof are also indicated for use in the treatment of conditions associated with rheumatism. It is believed that certain compounds of the present invention may act as disease-modifying antirheumatic agents. Such activity may be demonstrated by means of in vivo tests such as the antigen induced mouse arthritis test as described in WO 93/13097. The "term conditions associated with rheumatism" includes inter alia rheumatoid arthritis, osteoarthritis, osteoporosis, crystal arthropathies (e.g. gout), reactive arthritis, ankylosing spondylitis and psoriatic arthropathy.

Accordingly, in another aspect, the present invention provides a method of treating conditions associated with rheumatism comprising the administration of a therapeutically or prophylactically effective amount of a compound of formula I including pharmaceutically acceptable salts thereof (including the three excluded compounds and the compounds in the proviso) to a mammal in need thereof.

In yet another aspect, the present invention provides the use of a compound of formula I (including the three excluded compounds and the compounds in the proviso) in the manufacture of a medicament for use in treating conditions associated with inflammation, allergy, the immune system, rheumatism or neurological damage.

Processes for the preparation of compounds of formula I will now be described. These processes form a further aspect of the present invention. The processes are carried out at atmospheric pressure unless otherwise stated.

Compounds of formula I may be prepared by reacting a compound of formula IV

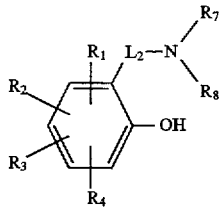

in which $R_1$, $R_2$, $R_3$, $R_4$, $R_7$, $R_8$ and $L_2$ are as previously defined, with a compound formula V

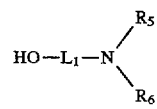

in which $R_5$, $R_6$ and $L_1$ are as previously defined, in the presence of a dialkyl azodicarboxylate, for example diethyl azodicarboxylate, and a phosphorus (III) reagent, for example triphenylphosphine, in the presence of an inert organic liquid which is preferably a solvent for the reactants, for example tetrahydrofuran, at a temperature in the range from 0° C. up to the boiling point of the inert organic liquid, for example 0°–250° C., preferably at a temperature in the range 0°–150° C.

Compounds of formula I may be prepared by reacting a compound of formula IV, as previously defined, with a compound of formula VI

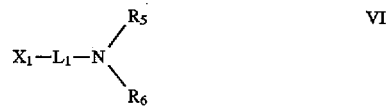

in which $R_5$, $R_6$ and $L_1$ are as previously defined and $X_1$ represents a leaving group, for example halo, optionally in the presence of a base, for example sodium hydride, in the presence of an inert organic liquid which is preferably a solvent for the reactants, for example N,N-dimethylformamide, at a temperature in the range from 0° C. up to the boiling point of the inert organic liquid, e.g. 0°–250° C., preferably by heating at a temperature in the range 20°–150° C.

Compounds of formula I in which $R_7$ and $R_8$ represent hydrogen may be prepared by reacting a compound of formula VII

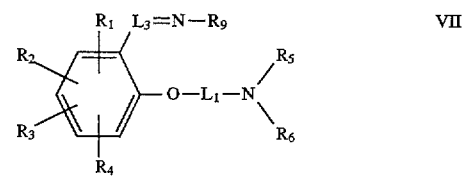

in which $R_1$, $R_2$, $R_3$, $R_4$, $R_5$, $R_6$ and $L_1$ are as previously defined and —$L_3$=N—$R_9$ represents a group which on reductive cleavage gives —$L_2$—$NH_2$, for example methoxyiminomethyl, with a reducing agent, for example borane, in an inert organic liquid which is preferably a solvent for the compound of formula VII, for example tetrahydrofuran, at a temperature in the range from 0° C. up to the boiling point of the inert organic liquid, e.g. 0°–250° C., preferably by heating at a temperature in the range 20°–150° C.

Compounds of formula I may be prepared by reacting a compound of formula VIII

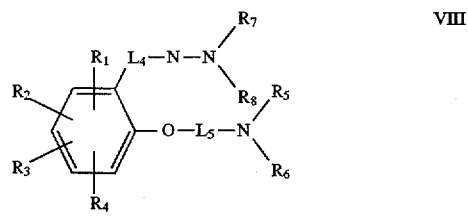

in which $R_1$, $R_2$, $R_3$, $R_4$, $R_5$, $R_6$, $R_7$ and $R_8$ are as previously defined and $L_4$ represents a group which on reduction gives $L_2$, for example a carbonyl group or a $C_{2-6}$ alkanoyl chain optionally substituted by one or more $C_{1-4}$ alkyl groups such that $L_4$ together with the nitrogen atom to which it is attached forms an amide linkage, and $L_5$ represents a group which on reduction gives $L_1$, for example a $C_{2-6}$ alkanoyl chain optionally substituted by one or more $C_{1-4}$ alkyl groups such that $L_5$ together with the nitrogen atom to which it is attached forms an amide linkage, with a reducing agent, for example borane, in an inert organic liquid which is preferably a solvent for the compound of formula VIII, for example tetrahydrofuran, at a temperature in the range from 0° C. up to the boiling point of the inert organic liquid, e.g. 0°–250° C., preferably by heating at a temperature in the range of 20°–150° C.

Compounds of formula I in which $R_7$ and $R_8$ represent hydrogen may be prepared by reacting a compound of formula IX

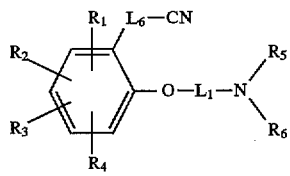

in which $R_1$, $R_2$, $R_3$, $R_4$, $R_5$, $R_6$ and $L_1$ are as previously defined and $L_6$ represents a bond or a $C_{1-5}$ alkylene chain optionally substituted by one or more $C_{1-4}$ alkyl groups, with a reducing agent, for example borane, in an inert organic liquid which is preferably a solvent for the compound of formula IX, for example tetrahydrofuran, at a temperature in the range from 0° C. up to the boiling point of the inert organic liquid, e.g. 0°–250° C., preferably by heating at a temperature in the range of 20°–150 C.

Compounds of formula I may be prepared by reacting a compound of formula X

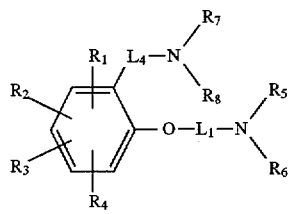

in which $R_1$, $R_2$, $R_3$, $R_4$, $R_5$, $R_6$, $R_7$, $R_8$ and $L_1$ are as previously defined and $L_4$ represents a group which on reduction gives $L_2$, for example a carbonyl group or a $C_{2-6}$ alkanoyl chain optionally substituted by one or more $C_{1-4}$ alkyl groups such that $L_4$ and the nitrogen atom to which it is attached form an amide linkage, with a reducing agent, for example borane, in an inert organic liquid which is preferably a solvent for the compound of formula X, for example tetrahydrofuran, at a temperature in the range from 0° C. up to the boiling point of the inert organic liquid, e.g. 0°–250° C., preferably by heating at a temperature in the range 20°–150° C.

Compounds of formula I may be prepared by reacting a compound of formula XI

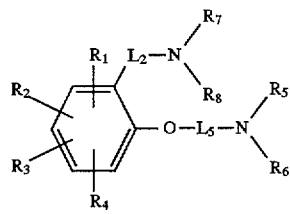

in which $R_1$, $R_2$, $R_3$, $R_4$, $R_5$, $R_6$, $R_7$, $R_8$ and $L_2$ are as previously defined and $L_5$ represents a group which on reduction gives $L_1$, for example a $C_{2-6}$ alkanoyl chain optionally substituted by one or more $C_{1-4}$ alkyl groups such that $L_5$ forms an amide linkage with the nitrogen atom to which it is attached, with a reducing agent, for example borane, in an inert organic liquid which is preferably a solvent for the compound of formula XI, for example tetrahydrofuran, at a temperature in the range from 0° C. up to the boiling point of the inert organic liquid, e.g. 0°–250° C., preferably by heating at a temperature in the range 20°–150° C.

Compounds of formula I in which $R_7$ represents hydrogen may be prepared by reacting a compound of formula XII

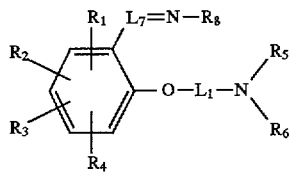

in which $R_1$, $R_2$, $R_3$, $R_4$, $R_5$, $R_6$ and $R_8$ are as previously defined and $L_7$=N—$R_8$ represents a group which on reduction gives $L_2$—NH$R_8$, with a reducing agent, for example sodium borohydride, in an inert organic liquid which is preferably a solvent for the compound of formula XII, for example an alcohol, eg ethanol, at a temperature in the range from 0° C. up to the boiling point of the inert organic liquid, e.g. 0°–250° C., preferably by heating at a temperature in the range of 15°–150° C.

Compounds of formula I may be prepared by reacting a compound of formula XIII

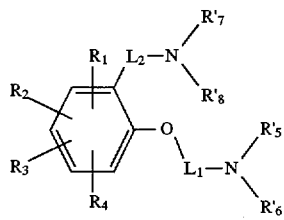

in which at least one of $R'_5$, $R'_6$, $R'_7$ and $R'_8$ represents; a group which on reduction gives $R_5$, $R_6$, $R_7$ and $R_8$ respectively, for example an acyl group e.g. an alkanoyl group, and the remainder (if any) represent $R_5$, $R_6$, $R_7$ and $R_8$ respectively, with a reducing agent, for example borane, in an inert organic liquid which is preferably a solvent for the compound of formula XIII, for example tetrahydrofuran, at a temperature in the range from 0° C. up to the boiling point of the inert organic liquid, e.g. 0°–250° C., preferably by heating at a temperature in the range of 15°–150° C.

Compounds of formula I may be prepared by reacting a compound of formula XIV

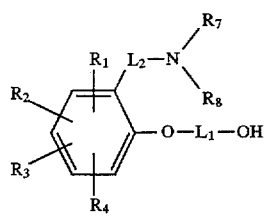

in which $R_1$, $R_2$, $R_3$, $R_4$, $R_7$, $R_8$, $L_1$ and $L_2$ are as previously defined, with a compound of formula XXV

HNR$_5$R$_6$      XXV in which $R_5$ and $R_6$ are as previously defined, in the presence of a dialkyl azodicarboxylate, for example diethyl azodicarboxylate, and a phosphorus (III) reagent, for example triphenylphosphine, in the presence of an inert organic liquid which is preferably a solvent for the reactants, for example tetrahydrofuran, at a temperature in the range of from 0° C. up to the boiling point of the inert organic liquid, for example 0°–250° C., preferably at a temperature in the range 0°–150° C.

Compounds of formula I may be prepared by reacting a compound of formula XXVI

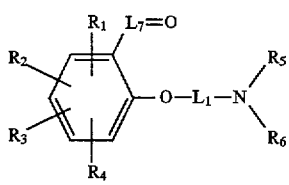

in which $R_1$, $R_2$, $R_3$, $R_4$, $R_5$, $R_6$ and $L_1$ are as previously defined and $L_7$ represents a group which on reduction gives $L_2$, with 1) an amine of formula $R_7R_8NH$, in the presence of an inert organic liquid which is preferably a solvent for the reactants, e.g. toluene, at a temperature in the range from 0° C. up to the boiling point of the inert organic liquid, for example 0°–250° C., preferably by heating at a temperature in the range of 15°–150° C., and then with 2) a reducing agent, for example sodium cyanoborohydride, in the presence of an inert organic liquid which is preferably a solvent for the reactants, e.g. ethanol, at a temperature in the range from 0° C. up to the boiling point of the inert organic liquid, for example 0°–250° C., preferably by heating at a temperature in the range of 15°–150° C.

Compounds of formula IV in which $L_2$ represents methylene may be prepared by reacting a compound of formula XVI

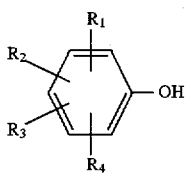

with formaldehyde or a formaldehyde equivalent, e.g. paraformaldehyde, with an amine of formula $R_7R_8NH$ or a salt thereof using the Mannich reaction, as known to those skilled in the art. It will be appreciated by those skilled in the art that when $R_7R_8NH$ is other than a secondary amine that further condensations may occur. Alternatively compounds of formula IV may be prepared by reacting a compound of formula XVI with a compound of formula $R_7R_8NCH_2NR_7R_8$ by methods known to those skilled in the art.

Certain compounds of formula V are commercially available or may be prepared by methods known to those skilled in the art.

Compounds of formula V, in which $R_6$ is as previously defined except for hydrogen, may be prepared by reacting a compound of formula XVII

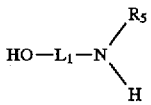

in which $L_1$ and $R_5$ are as previously defined with a compound of formula $R_6$-$X_2$ in which $X_2$ represents a leaving group, for example halo preferably chloro or bromo, and $R_6$ is other than hydrogen, optionally in the presence of an inert organic liquid which is preferably a solvent for the reactants, for example a hydrocarbon, e.g. xylene, at a temperature in the range from 0° C. up to the boiling point of the inert organic liquid, for example 0°–250° C., preferably 15°–150° C.

Compounds of formula VI are commercially available or may be prepared by methods known to those skilled in the art, for example by reacting a compound of formula V with a halogenating agent e.g. thionyl chloride at a temperature in the range –50°–150° C., preferably –25°C. to 100° C., optionally in the presence of an inert organic liquid which is preferably a solvent for the reactants, for example a halogenated hydrocarbon, for example chloroform.

Compounds of formula VII may be prepared by reacting a compound of formula XVIII

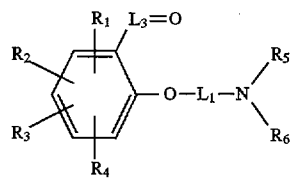

with a compound of formula $H_2N$—$R_9$ in which $R_9$ is a reductively cleavable group, for example alkoxy e.g. methoxy, for example by heating together optionally in the presence of an inert organic liquid which is preferably a solvent for the reactants, for example an alcohol e.g. ethanol, optionally in the presence of a base, for example pyridine, at a temperature in the range from 0° C. up to the boiling point of the inert organic liquid, e.g. 0°–250° C., preferably by heating at a temperature in the range 20°–150° C.

Compounds of formula VIII may be prepared by reacting a compound of formula XIX

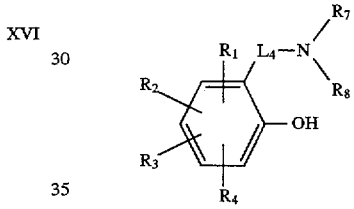

in which $R_1$, $R_2$, $R_3$, $R_4$, $L_4$, $R_7$ and $R_8$ are as defined previously with a compound of formula VI(a)

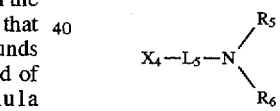

in which $L_5$ is as previously defined and $X_4$ represents a leaving group, for example halo, preferably chloro or bromo, optionally in the presence of a base, for example sodium hydride, optionally in the presence of an inert organic liquid which is preferably a solvent for the reactants, for example tetrahydrofuran, at a temperature in the range from 0° C. up to the boiling point of the inert organic liquid, e.g. 0°–250° C., preferably by heating at a temperature in the range 20°–150° C.

Compounds of formula IX may be prepared by reacting a compound of formula XX

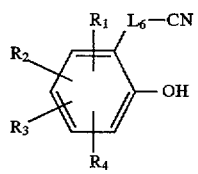

with a compound of formula VI in a similar manner to the preparation of a compound of formula I by the reaction of a compound of formula IV with a compound of formula VI.

Compounds of formula IX may also be prepared by reacting a compound formula XXI

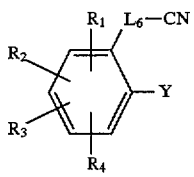

XXI in which Y represents halo, preferably fluoro, with a compound of formula V or a salt thereof in the presence of a base, e.g. sodium hydride, preferably in the presence of an inert organic liquid which is preferably a solvent for the starting materials, e.g. N,N-dimethylformamide, at a temperature in the range from 0° C. up to the boiling point of the solvent e.g. 0°–250° C. preferably 15°–150° C. It will be understood by those skilled in the art that if any of $R_1$, $R_2$, $R_3$ or $R_4$ represent halo then for optimum results Y must be more susceptible to nucleophilic displacement than $R_1$, $R_2$, $R_3$ or $R_4$. It will also be understood by those skilled in the art that when $L_6$ is other than a bond then more forcing reaction conditions may be required unless one or more of the substituents $R_1$–$R_4$ activates Y to nucleophilic displacement.

Compounds of formula X may be prepared by reacting a compound of formula XIX

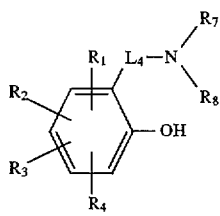

XIX in which $R_1$, $R_2$, $R_3$, $R_4$, $L_4$, $R_7$ and $R_8$ are as previously defined, with a compound of formula V, in a similar manner to the preparation of a compound of formula I by the reaction of a compound of formula IV with a compound of formula V.

Compounds of formula X may also be prepared by reacting a compound of formula XXIII

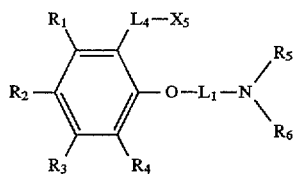

XXIII in which $X_5$ represents a leaving group, for example halo or an acyloxy group, with a compound of formula $R_7R_8NH$ by methods known to those skilled in the art.

Compounds of formula XI may be prepared by reacting a compound of formula XXIV

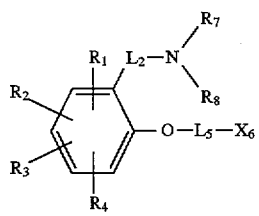

XXIV in which $X_6$ represents a leaving group, for example halo or an acyloxy group, with an amine of formula XXV

HNR$_5$R$_6$  XXV by methods known to those skilled in the art.

Compounds of formula XII may be prepared by reacting a compound of formula XXVI in which the substituents are as previously defined with a compound of formula $R_8NH_2$ by methods known to those skilled in the art.

Compounds of formula XIII may be prepared from compounds of formula I by methods known to those skilled in the art, or by methods analogous to those previously described for the preparation of formula I.

Compounds of formula XIV may be prepared from compounds of formula IV by methods known to those skilled in the art.

Compounds of formula XVI and compounds of formula XVII are commercially available or may be prepared by methods known to those skilled in the art.

Compounds of formula XVIII may be prepared by reacting a compound of formula XXVII

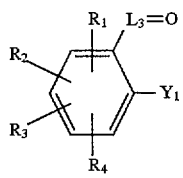

XXVII in which $Y_1$ represents a leaving group, for example halo, preferably fluoro with a compound of formula V or a salt thereof by methods analogous to those described for the preparation of a compound of formula IX from a compound of formula XXI and a compound of formula V with the remarks about the susceptibility of Y to nucleophilic displacement applying equally to $Y_1$.

Compounds of formula XIX may be prepared by reacting a compound of formula XXVIII

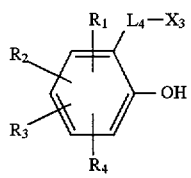

XXVII in which $X_3$ represents a leaving group, for example halo or an acyloxy group, with a compound of formula $R_7R_8NH$ by methods known to those skilled in the art.

Compounds of formula XX and XXI may be prepared by methods known to those skilled in the art.

Compounds of formula XXIII, XXIV, XXV, XXVI, XXVII and XXVIII are commercially available or may be prepared by methods known to those skilled in the art.

It will be appreciated by those skilled in the art that in cases where a substituent is identical with or similar to a functional group which is being modified in one of the above processes that these substituents will require protection before the process is undertaken followed by deprotection after the process. Otherwise competing side-reactions will occur. Alternatively another of the processes described above, in which the substituent does not interfere, may be used.

It will be appreciated by those skilled in the art that the substituents specified for $R_1$, $R_2$, $R_3$ and $R_4$ may be interconverted by methods known to those skilled in the art. For example a cyano group may be hydrolysed to a carbamoyl group or an alkoxy group may be cleaved to give a hydroxy group. Also certain compounds of formula I may be converted into other compounds of formula I as indicated below.

Compounds of formula I in which at least one of $R_5$, $R_6$, $R_7$ or $R_8$ represents a group other than hydrogen may be prepared by alkylating a compound of formula I in which at least one of $R_5$, $R_6$, $R_7$ and $R_8$, respectively, represents hydrogen, either a) directly using an alkylating agent of formula $R_5X$, $R_6X$, $R_7X$ or $R_8X$, respectively, in which X represents a leaving group, for example halo, in the presence of an organic liquid which is preferably a solvent for the reactants at a temperature in the range 0°–150° C., optionally in the presence of a base, or b) by reductive alkylation, comprising reaction with an aldehyde or a ketone, for example formaldehyde or benzaldehyde, in the presence of a reducing agent, for example formic acid, sodium borohydride, sodium cyanoborohydride or hydrogen in the presence of a catalyst, optionally in the presence of an inert organic liquid, which is preferably a solvent for the reactants, at a temperature in the range 0°–250° C., preferably in the range 15°–150° C.

In a preferred process, compounds of formula I in which $R_1$, $R_2$, $R_3$, $R_4$, $L_1$ and $L_2$ are as previously defined, $R_5$, $R_7$ and $R_8$ represent methyl and $R_6$ represents benzyl may be prepared by reacting a compound of formula I in which $R_1$, $R_2$, $R_3$, $R_4$, $L_1$ and $L_2$ are as previously defined, $R_6$ represents benzyl, $R_7$ and $R_8$ represent hydrogen and $R_5$ represents hydrogen or methyl, with formaldehyde and formic acid at a temperature in the range 0°–150° C.

In a further preferred process, compounds of formula I in which $R_1$, $R_2$, $R_3$, $R_4$, $L_1$ and $L_2$ are as previously defined, $R_5$, $R_7$ and $R_8$ represent methyl and $R_6$ represents benzyl may be prepared by reacting a compound of formula I in which $R_1$, $R_2$, $R_3$, $R_4$, $L_1$ and $L_2$ are as previously defined, $R_5$, $R_7$ and $R_8$ represent methyl and $R_6$ represents hydrogen, with benzaldehyde in the presence of a reducing agent, for example sodium borohydride, in the presence of an inert organic liquid, which is preferably a solvent for the starting material, at a temperature in the range 0°–150° C.

The compounds of formula I are antiinflammatory agents and may show therapeutic activity at a dose of 200 mg/kg or lower in standard laboratory animals. The therapeutic activity of compounds of formula I has been demonstrated by Test A and one or more of Tests B, C and D.

Test A was carried out in the following way:

Inhibition of Arachidonic Acid Release from Zymosan Stimulated Macrophages

Female MF1 mice (weighing 20 to 25 g) were killed using a rising concentration of $CO_2$. The mice were laid on their backs and the abdomens wiped with 70% alcohol. The skin was pulled back, exposing the peritoneal wall. Medium A (5 ml) (see below) was injected into the peritoneal cavity of each mouse followed by approximately 1 ml of air using a 20 ml syringe and a 21 G×40 mm needle in order to form a suspension of macrophage cells. The medium and cells were then removed using a 19 G×40 mm needle. The resulting suspension was returned to a sterile beaker kept on ice. The extracts from all the mice were pooled and this pooled cell suspension was counted using a Coulter counter and adjusted to a final cell count of $1$–$1.3 \times 10^6$ cells/ml prior to labelling with [$^3$H]-arachidonic acid. Typically five mice provided sufficient cells for each multiwell plate.

Sufficient [$^3$H]-arachidonic acid in ethanol to give a final concentration of 1.6 µCi/ml (equivalent to 40 µCi/plate) was blown to dryness under nitrogen. The arachidonic acid was then resuspended in 1 or 2 ml of the cell suspension which was then mixed with the remainder of the cell suspension in a centrifuge bottle. The labelled cell suspension was then plated out into sterile plastic 96 flat-bottomed well plates (250 µl per well) and incubated overnight at 37° C. in a moist atmosphere of 5% $CO_2$, 95% air.

The following day, non-adherent cells were removed by washing 3 times with sterile phosphate buffered saline (PBS). The adherent peritoneal macrophages were then cultured for a further 24 hours in the presence or absence of drugs, in medium B (see below) at 37° in a 5% $CO_2$ atmosphere in order to measure the effects of drugs on the spontaneous release of arachidonic acid in the absence of stimulus. After this incubation, supernatants were removed to give medium 1 and stored in sealed multi-well plates at 4° C. prior to scintillation counting. Drugs which potentiated spontaneous release of arachidonic acid (125% of controls) were deemed to be toxic at the concentration at which this phenomenon occurred. The supernatants were replaced by fresh medium C containing fresh drug and a stimulus. Three drugs were tested at six concentrations (100, 50, 20, 10, 5 and 1 µM) in replicates of four on each plate. The other wells contained controls consisting of a positive control (e.g. dexamethasone), medium (B) only and medium C only.

Incubation was then continued for a further 5 hours, whereupon the supernatants were collected to give medium 2 and the adherent cells washed with PBS. The cells were then lysed with 100 µl of 0.1% TRITON® X100 in a 0.1% solution of bovine serum albumin in 0.9% saline and mechanically disrupted to give cell lysates. These supernatants (medium 2) and cell lysates (Cells) were also stored in sealed multi-well plates at 4° C. prior to scintillation counting. 200 µl aliquots of media, or 100 µl aliquots of cells were counted using 2 ml of OPTIPHASE "HIGH SAFE" (Trademark of LKB) as scintillant.

Calculation of results

The percentage of arachidonic acid released was calculated using the mean values for each group of 4 wells in the following equation.

$$\% \text{ Release} = \frac{\text{cpm in medium 2}}{\text{cpm in medium 2 + cpm in cell lysate}} \times 100$$

cpm = counts per minute

The value for the arachidonic acid release in the absence of stimulus (spontaneous, cpm of medium 2) from cells which had been exposed to neither stimulus nor drug was subtracted from all equivalent values (cpm media 2, stimulated with or without drug) to give the net stimulated release. The percentage inhibition of arachidonic acid release caused by a drug may then be calculated using the following equation.

$$\% \text{ Inhibition} = 100 - \frac{\text{net stimulated release in presence of drug} \times 100}{\text{net stimulated release in absence of drug}}$$

Compounds of formula I were tested at six concentrations (100, 50, 20, 10, 5 and 1 µM) and $IC_{50}$ values calculated. Compounds with $IC_{50}$ values <100 µM are considered to be active. Advantageous compounds have an $IC_{50}$ value <50 µM.

Medium A (for peritoneal lavage)

To a sterile 100 ml measuring cylinder was added:—40 ml TC199 with Earle's salts (tenfold concentrate) (ICN); 4 ml heat inactivated swine serum (ICN); 10 ml sodium bicarbonate (7.5% in sterile water); 0.4 ml antibiotics solution (60 mg/ml benzylpenicillin+100 mg/ml streptomycin) and 0.72 ml heparin (5000 U/ml). This mixture was transferred to sterile flask and made up to 400 ml with sterile water.

Medium B (for cell culture)

To a sterile 250 ml measuring cylinder was added:—65 ml TC 199 (tenfold concentrate) with Earle's salts (ICN); 6.5 ml heat inactivated swine serum; 16.25 ml sodium bicarbonate (7.5% in sterile water); 0.65 ml antibiotics solution as above and 65 mg glutamine. This mixture was transferred to a sterile beaker and made up to 650 ml with sterile water.

Medium C=medium B+stimulant (zymosan)

The zymosan stimulant was prepared as follows:—zymosan (200 mg) (supplied by Sigma) was added to PBS (20 ml). The mixture was boiled for 30 minutes and the volume restored to 20 ml with water. The zymosan was harvested by centrifugation at 500×g for 5 minutes, washed twice by resuspension in PBS (10 ml) and centrifugation. After the final separation, the zymosan was resuspended in 20 ml PBS and stored as 1 ml aliquots at −20° C.

650 ml medium B containing 15 ml zymosan=12.5 particles per cell was made up and then stored in 3 ml aliquots in freezer.

Test B was carried out in the following way:
Carrageenan-induced rat paw oedema test Female rats, weight range 125–150 g were fasted overnight. One of the hind legs of each animal was marked with a line at the connection between the cuboid/navicular and calcaneus/talus bones. Groups of six rats were orally dosed at 10 ml/kg, in random order, with a given dose of the test compound given as a solution or suspension in 10% (w/v) aqueous acacia solution.

One hour after dosing, 0.1 ml of 1% (w/v) sterile carrageenan λ in normal saline was injected deeply into the plantar surface of the marked hind foot of each rat. The volume of the foot (up to the marked line) was measured immediately after injection using duplicate water displacement readings. Three hours after injection the foot volume was measured again and the percentage increase in foot volume relative to the initial reading was calculated.

The increase in foot volume (i.e. the degree of oedema) in drug treated animals when compared with that in the drug untreated control gave the degree of inhibition of paw oedema by the drug.

Compounds were considered to be active in this test if they produced a statistically significant (typically 20% or greater) inhibition of paw oedema in at least two out of three tests after oral dosing at 100 mg/kg. Statistical significance was assessed using the Student's t test for single dose studies and Dunnett's test for multiple dose studies. More advantageous compounds were active in both Tests A and B.

TABLE 1

| Example | Test A IC$_{50}$ μM | Test B % inhibition at 100 mg/kg |
|---|---|---|
| 1 | 15 | 70 |
| 2 | 65 | |
| 3 | 20 | 52 |
| 4 | 60 | |
| 5 | 12 | 6 |
| 6 | 15 | 18 |
| 7 | 20 | 18 |
| 8 | 13 | 23 |
| 9 | 9 | 56 |
| 10 | 47 | |
| 11 | 10 | 47 |
| 12 | 8 | 68 |
| 13 | 8 | 70 |
| 14 | 45 | |
| 15 | 60 | |
| 16 | 26 | |
| 17 | 13 | 36 |
| 18 | 24 | |
| 19 | 65 | |
| 20 | 36 | 64 |
| 21 | 22 | 31 |
| 22 | 14 | 26 |
| 23 | 62 | |
| 24 | 50 | |
| 25 | 30 | 22 |

TABLE 1-continued

| Example | Test A IC$_{50}$ μM | Test B % inhibition at 100 mg/kg |
|---|---|---|
| 26 | 33 | |
| 27 | 34 | |
| 28 | 18 | |
| 29 | 15 | |
| 30 | 74 | |
| 31 | 39 | 19 |
| 32 | 39 | 0 |
| 33 | 16 | |
| 34 | 35 | |
| 35 | 33 | |
| 36 | 3 | |
| 37 | 12 | |

TEST C

The most advantageous compounds of formula I were active in Test A and also in the following test. Carrageenan-induced pleurisy in rats was carried out as described by Ackerman et al. J. Pharmacol. Exp. Therap. 1980, 215, 588–595. Migrating leukocytes were harvested by lavage of the thoracic cavity 72 h after injection of 0.3 ml 1% λ-carrageenan in sterile isotonic saline. Test compounds were administered p.o. at the time of challenge and 24 h and 48 h thereafter.

For example the final products of Examples 3, 6, 8, 11, 12, 13, 20 and 22 were active at 30 mg/kg in Test C and the final products of Examples 1, 14, 17, 21, 33, 35, 36 and 37 were active at 10 mg/kg or less in Test C.

Compounds which exhibit activity in both Tests A and C possess an advantageous profile of pharmacological activity unknown in commercially available antiinflammatory drugs and it is highly likely that such compounds possess significant advantages in terms of increased efficacy and/or reduced side-effects compared with known commercially available antiinflammatory drugs.

TEST D

Compounds of formula I suitable for the treatment of asthma were active in the three tests above and also in the late phase of the following test. Early and late phase bronchoconstriction in guinea-pigs following antigen challenge was determined by a variation of the method described by Hutson et al. Am. Rev. Respir. Dis. 1988, 137, 548–557. Guinea-pigs were sensitised by a single i.p. injection of 10 μg ovalbumin and challenged 15 to 17 days later by exposure to aerosolized antigen (4%) for five minutes, following pretreatment with mepyramine to prevent anaphylaxis. Changes in lung function were determined by whole body plethysmography at various times after challenge. Test compounds were administered p.o. 24 h and 2 h prior to challenge.

TEST E

The therapeutic activity of certain compounds of the present invention has also been demonstrated by an in vitro mixed lymphocyte reaction performed as described in WO 95/00507.

The invention is illustrated by the following non-limitative Examples in which compositions of mixed solvents are given by volume. Novel compounds were characterised by one or more of the following: elemental analysis, nuclear magnetic resonance (NMR), infra-red and mass spectroscopy. Temperatures are given in degrees Celsius. The abbreviations HPLC (high performance liquid chromatography), THF (tetrahydrofuran), DMF (dimethylformamide), DMSO (dimethyl sulphoxide), Amt (Amount), Vol (Volume), Temp (Temperature), Ex (Example), IMS (industrial methylated spirit), Wt. (weight) have been used in the Examples.

EXAMPLE 1

N-Benzyl-N-methylethanolamine (5.25 ml), triphenylphosphine (8.48 g) and diethyl azodicarboxylate (5.09 ml) were added to a solution of 3-chloro-2-(dimethylaminomethyl)phenol (6.0 g) in dry THF (200 ml) at ambient temperature with stirring under nitrogen. The mixture was stirred at ambient temperature for 24 hours and then evaporated to dryness under reduced pressure at 30° C. The residue was dissolved in 2M hydrochloric acid, washed with ethyl acetate, and then basified with concentrated sodium hydroxide solution. The mixture was extracted with dichloromethane to give an oil which was distilled under vacuum in a Kugelrohr. The higher boiling fraction which boiled at 140° C. at 0.01 mbar was dissolved in ether and treated with ethereal hydrogen chloride. The mixture was filtered and the solid collected was recrystallised from propan-2-ol to give 2-[2-(N-benzyl-N-methylamino)ethoxy]-6-chloro-N,N-dimethylbenzylamine dihydrochloride, m.p. 238°–239° C.

Examples 2–18 were prepared in a similar manner to Example 1 as summarised in Table 1 in which a compound of formula IV in which $L_2$ represents methylene, was reacted with a compound of formula V. The substituents on IV and the amounts of the reactants are given in the Table. In $R_1$–$R_4$, $R_1$, $R_2$, $R_3$ and $R_4$ are hydrogen unless otherwise stated. In examples 2, 10, 14, 17 and 18 conversion into the dihydrochloride salt was omitted. In examples 2–18, V was N-benzyl-N-methylethanolamine with the exception of the following Examples:

9: V was N-benzylethanolamine;

10: V was 4-(N-2-hydroxyethyl-N-methylaminomethyl)benzonitrile;

12: V was N-benzyl-N-methylpropanolamine;

14: V was N-(2-chlorobenzyl)-N-methylethanolamine;

16: V was 2-piperidinoethanol; and

17: V was N-(4-chlorobenzyl)-N-methylethanolamine;

Notes

1. The oil, obtained after removal of the dichloromethane, was stirred with petroleum ether b.p. 60°–80° C. and then the petroleum ether was decanted away from insoluble material, dried and evaporated to give an oil. Low boiling impurities were distilled off at 80°–100° C. at 0.13 mbar. The residue was dissolved in ether and treated with ethereal hydrogen chloride. The product was collected by filtration.

2. The oil obtained after removal of the dichloromethane was dissolved in ether and treated with ethereal hydrogen chloride. The mixture was filtered and the filtrate evaporated under reduced pressure to give a solid residue which was triturated with AR acetone, filtered and dried to give the product.

TABLE 1

| Ex. | IV | | | THF Vol (ml) | V Vol (ml) | TPP Wt. (g) | DEAD Vol (ml) | Time (hours) | B.P. OF PRODUCT |
| | $R_1$–$R_4$ | $R_7$ | $R_8$ Wt (g) | | | | | | |
|---|---|---|---|---|---|---|---|---|---|
| 2 | 6-Cl | $CH_3$ | $CH_3$ 4.00 | 200 | 3.56 | 5.67 | 3.40 | 24 | 155° C./0.13 mbar |
| 3 | 4-F | $CH_3$ | $CH_3$ 5.58 | 250 | 5.25 | 8.51 | 4.61 | 16 | 110° C./0.01 mbar |
| 4 | 4-CN | $CH_3$ | $CH_3$ 11.10 | 200 | 10.23 | 16.52 | 9.92 | 96 | NOTE 1 |
| 5 | 4,5-$Cl_2$ | $CH_3$ | $CH_3$ 3.31 | 70 | 2.44 | 3.94 | 2.37 | 96 | NOTE 1 |
| 6 | 5-Cl | $CH_3$ | $CH_3$ 9.28 | 150 | 8.94 | 13.11 | 7.87 | 72 | NOTE 1 |
| 7 | 4-$CF_3$ | $CH_3$ | $CH_3$ 9.56 | 150 | 8.94 | 13.11 | 7.87 | 72 | NOTE 1 |
| 8 | 3,4-NAP | $CH_3$ | $CH_3$ 12.50 | 250 | 10.09 | 16.30 | 9.78 | 120 | NOTE 1 |
| 9 | 4-Cl | $CH_3$ | $CH_3$ 9.28 | 150 | 7.10 | 13.11 | 7.87 | 24 | 140° C./0.06 mbar |
| 10 | 4-Cl | $CH_3$ | $CH_3$ 23.00 | 500 | 11.8 | 16.26 | 9.75 | 48 | 200° C./0.13 mbar |
| 11 | 4-Cl | —$(CH_2)_5$— | | 7.45 | 100 | 5.36 | 8.66 | 5.20 | 16 | 140° C./0.01 mbar |
| 12 | 4-Cl | $CH_3$ | $CH_3$ 6.13 | 100 | 5.91 | 8.66 | 5.20 | 16 | 150° C./0.01 mbar |
| 13 | 3,4-$Cl_2$ | $CH_3$ | $CH_3$ 8.65 | 100 | 6.39 | 10.31 | 6.19 | 72 | NOTE 2 |
| 14 | H | $CH_3$ | $CH_3$ 7.57 | 200 | 10.0 | 13.15 | 7.9 | 96 | 150° C./0.01 mbar † |
| 15 | 3-CN | $CH_3$ | $CH_3$ 10.57 | 200 | 9.91 | 15.74 | 9.45 | 96 | 170° C./0.01 mbar † |
| 16 | 4-Cl | $CH_3$ | $CH_3$ 8.00 | 500 | 5.56 | 11.30 | 6.80 | 144 | 150° C./0.06 mbar † |
| 17 | H | $CH_3$ | $CH_3$ 7.60 | 500 | 10.0 | 13.14 | 7.9 | 72 | 200° C./0.65 mbar |
| 18 | 5-$OCH_3$ | $CH_3$ | $CH_3$ 19.40 | 250 | 20.0 | 28.85 | 19.16 | 168 | NOTE 3 |

3,4-NAP represents 3,4(—CH=CH—CH=CH—)
TPP represents triphenylphosphine
DEAD represents diethyl azodicarboxylate
B.P. represents boiling point Notes continued After the reaction mixture had been evaporated to dryness, ether was added to the residue and the mixture was filtered. The filtrate was extracted with dilute hydrochloric acid and the hydrochloric acid layer was washed with dichloromethane. The acid layer was then basified with 2M sodium hydroxide solution and extracted with dichloromethane to give an oil which was distilled and the product acidified as in Example 1.

3. The starting material IV was a mixture of isomers. The oil obtained after removal of the dichloromethane was purified by flash column chromatography on silica using dichloromethane/methanol (9:1) as the mobile phase. Fraction 3 which distilled at 160° C. at 0.65 mbar was identified by $^1$H NMR spectroscopy.

The compounds prepared in Examples 2–18 are listed below.

EXAMPLE 2

2-[2-(N-Benzyl-N-methylamino)ethoxy]-3-chloro-N,N-dimethylbenzylamine, b.p. 150° C. at 0.13 mbar.

EXAMPLE 3

2-[2-(N-Benzyl-N-methylamino)ethoxy]-5-fluoro-N,N-dimethylbenzylamine dihydrochloride, m.p. 198°–199° C.

EXAMPLE 4

4-[2-(N-Benzyl-N-methylamino)ethoxy]-3-(dimethylaminomethyl)benzonitrile dihydrochloride hemihydrate, m.p. 179°–180° C.

EXAMPLE 5

2-[2-(N-Benzyl-N-methylamino)ethoxy]-4,5-dichloro-N,N-dimethylbenzylamine dihydrochloride dihydrate, m.p. 134° C.

EXAMPLE 6

2-[2-(N-Benzyl-N-methylamino)ethoxy]-4-chloro-N,N-dimethylbenzylamine dihydrochloride, m.p. 195°–197 ° C. (from propan-2-ol).

EXAMPLE 7

2-[2-(N-Benzyl-N-methylamino)ethoxy]-N,N-dimethyl-5-trifluoromethylbenzylamine dihydrochloride. m.p. 207°–209° C. (from propan-2-ol).

EXAMPLE 8

N-Benzyl-2-[1-(dimethylaminomethyl)naphth-2-yloxy]-N-methylethylamine dihydrochloride. m.p. 230°–231° C. (from propan-2-ol).

EXAMPLE 9

2-[2-(Benzylamino)ethoxy]-5-chloro-N,N-dimethylbenzyl-amine dihydrochloride. m.p. 175° C. (from propan-2-ol).

EXAMPLE 10

4-{N-[2-(4-Chloro-2-dimethylaminomethylphenoxy)ethyl]-N-[methyl]aminomethyl}benzonitrile hemihydrate as an oil not distilled.

EXAMPLE 11

N-Benzyl-2-[4-chloro-2-(piperidinomethyl)phenoxy]-N-methylethylamine dihydrochloride. m.p. 228°–230° C. (after trituration with acetone).

EXAMPLE 12

2-[3-(N-Benzyl-N-methylamino)propoxy]-5-chloro-N,N-dimethylbenzylamine dihydrochloride. m.p. 213°–215° C.

EXAMPLE 13

2-[2-(N-Benzyl-N-methylamino)ethoxy]-5,6-dichloro-N,N-dimethylbenzylamine dihydrochloride hemihydrate, m.p. 207°–8° C.

EXAMPLE 14

2-{2-[N-(2-Chlorobenzyl)-N-methylamino]ethoxy}-N,N-dimethylbenzylamine, b.p. 150° C. at 0.13 mbar.

EXAMPLE 15

3-[2-(N-Benzyl-N-methylamino)ethoxy]-2-(dimethylaminoethyl) benzonitrile dihydrochloride, m.p. 243°–245° C.

EXAMPLE 16

5-Chloro-2-(2-piperidinoethoxy)-N,N-dimethylbenzylamine dihydrochloride, m.p. 237°–239° C.

EXAMPLE 17

2-{2-[N-(4-Chlorobenzyl)-N-methylamino]ethoxy}-N,N-dimethylbenzylamine, b.p. 200° C. at 0.52 mbar.

EXAMPLE 18

2-[2-(N-Benzyl-N-methylamino)ethoxy]-4-methoxy-N,N-dimethylbenzylamine, b.p. 160° C. at 0.65 mbar.

EXAMPLE 19

A solution of 2-(N,N-dimethylaminomethyl)phenol (10.0 g, which contains 30% phenol by weight) in DMF (10 ml) was added dropwise with stirring to a suspension of sodium hydride (3.14 g, 60% dispersion in mineral oil) in DMF (75 ml) at ambient temperature under nitrogen. After the addition the mixture was stirred at ambient temperature for 30 minutes. A solution of 2-chloro-N,N-diethylethylamine in toluene (70 ml) [prepared by dissolving the hydrochloride (14.8 g) in water (20 ml), adding aqueous sodium hydroxide (5M) to basify the mixture and then extracting the mixture with toluene 3×20 ml, drying, filtering and then making up to 70 ml as required] was added dropwise over a period of 2 minutes and the resulting mixture heated on a steam bath for 18 hours under nitrogen. The mixture was poured into ice/water (500 ml) and sodium hydroxide solution was added until the mixture was basic (pH=14). The mixture was extracted with ether to give a residue which was distilled under vacuum. The highest boiling fraction (b.p. 105°–110° C. at 0.6 mbar) was dissolved in ether and acidified with ethereal hydrogen chloride. The solvent was removed under reduced pressure. The residue was dissolved in propan-2-ol and ether added to induce precipitation. The solid was collected by filtration and recrystallised from propan-2-ol to give 2-(2-diethylaminoethoxy)-N,N-dimethylbenzylamine dihydrochloride, m.p. 213°–214° C.

Examples 20–25 were prepared in a similar manner to Example 19. A compound of formula IV, in which $L_2$ represents methylene, was reacted with a compound of formula VI, in which $L_1$ represents a group of formula —$(CH_2)_m$— and $X_1$ represents chloro, as summarised in Table 2. The hydrochloride salt of VI was basified and extracted into toluene as described in Example 19. The substituents and the weights of the reactants are given in Table 2. The substituents $R_1$, $R_2$, $R_3$ and $R_4$ each represent hydrogen unless otherwise stated. The starting material, IV, in examples 20, 23 and 24 contained 30% by weight of phenol.

TABLE 2

| Ex | $R_1$–$R_4$ | IV $R_7$ | $R_8$ | Wt (g) | NaH Wt (g) | DMF Vol (ml) | m | VI. HCl $R_5$ | $R_6$ | Wt (g) | Tol Vol (ml) | B.P. (°C.) of Product |
|---|---|---|---|---|---|---|---|---|---|---|---|---|
| 20 | H    | $CH_3$ | $CH_3$ | 15.0 | 4.71 | 120 | 2 | $CH_3$   | $CH_2Ph$ | 28.4  | 100 | 156–162/0.5 mbar |
| 21 | 4-Cl | $CH_3$ | $CH_3$ | 8.0  | 1.73 | 70  | 2 | $CH_3$   | $CH_2Ph$ | 10.44 | 90  | 190–200/13 mbar[1] |
| 22 | 4-Cl | $CH_3$ | $CH_3$ | 8.0  | 1.73 | 70  | 2 | $CH_3$   | $CH_3$   | 6.77  | 90  | NOTE 2 |
| 23 | H    | $CH_3$ | $CH_3$ | 15.0 | 4.68 | 120 | 2 | $CH_3$   | $CH_3$   | 18.5  | 70  | 82–90/0.6 mbar |
| 24 | H    | $CH_3$ | $CH_3$ | 15.0 | 4.68 | 120 | 3 | $CH_3$   | $CH_3$   | 20.22 | 70  | 100–120/0.6 mbar |
| 25 | 4-Cl | $CH_3$ | $CH_3$ | 8.0  | 1.73 | 70  | 2 | $C_2H_5$ | $C_2H_5$ | 8.2   | 75  | 190–200/13 mbar |

Wt = weight : Vol = volume : Tol = toluene
Notes
1. The crude hydrochloride salt was recrystallised from IMS. The first crop of solid was discarded and the filtrate was evaporated to give a residue which was recrystallised twice from propan-2-ol to give the product.
2. The oil obtained after extractive workup was purified by flash column chromatography on silica using methanol/triethylamine (98:2) as the mobile phase. The second fraction was converted into the hydrochloride salt as in Example 19.

EXAMPLE 20

2-[2-(N-Benzyl-N-methylamino)ethoxy]-N,N-dimethylbenzylamine dihydrochloride, m.p. 212°–213° C.

EXAMPLE 21

2-[2-(N-Benzyl-N-methylamino)ethoxy]-5-chloro-N,N-dimethylbenzylamine dihydrochloride, m.p. 195°–196° C.

EXAMPLE 22

5-Chloro-2-(2-dimethylaminoethoxy)-N,N-dimethylbenzylamine dihydrochloride, m.p. 225°–226° C.

EXAMPLE 23

The crude hydrochloride salt was triturated with acetone and filtered to give 2-(2-dimethylaminoethoxy)-N,N-dimethylbenzylamine dihydrochloride, m.p. 245°–247° C.

EXAMPLE 24

The crude hydrochloride salt was triturated with acetone and filtered to give N,N-dimethyl-2-(3-dimethylaminopropoxy) benzylamine dihydrochloride, m.p. 235°–236° C.

EXAMPLE 25

The oil obtained after distillation was purified by flash column chromatography on silica using methanol and then methanol/triethylamine (9:1) as the mobile phase to give 5-chloro-2-(2-dimethylaminoethoxy)-N,N-dimethylbenzylamine as an oil.

EXAMPLE 26

A solution of methyl 4-hydroxy-3-(dimethylaminomethyl)benzoate (9.86 g) in dry THF (100 ml) was added dropwise with stirring to a suspension of sodium hydride (2.00 g, 60% dispersion in mineral oil) in dry THF under nitrogen. Further dry THF (200 ml) was added and the mixture stirred at ambient temperature for 30 minutes. A solution of N-benzyl-2-chloro-N-methylethylamine (9.18 g) in dry THF (75 ml) was added dropwise and the mixture stirred at ambient temperature for 18 hours. The mixture was then boiled under reflux for 5 hours. Since no reaction appeared to have occurred, some solvent was boiled off (approximately 100 ml) and replaced by dry DMF (100 ml). The mixture was boiled under reflux for 18 hours. The mixture was cooled to ambient temperature and water (100 ml) was added cautiously. The mixture was evaporated to dryness and the residue was treated with dilute sodium hydroxide solution and then extracted with dichloromethane to give an oil. The oil was dissolved in ether and treated with ethereal hydrogen chloride solution. The mixture was filtered to give a solid which was recrystallised from ethanol to give an impurity, but the filtrate was evaporated to dryness to give a residue which was triturated with AR acetone and filtered to give methyl 4-[2-(N-benzyl-N-methylamino)ethoxy]-3-(dimethylaminomethyl) benzoate dihydrochloride hydrate, m.p. 217°–219° C.

EXAMPLE 27

A solution of 2-[2-(N-benzyl-N-methylamino)ethoxy]-5-methoxy-O-methylbenzaldehyde oxime (5.19 g) (prepared from the aldehyde in a similar manner to Example 28) in THF (50 ml) was treated with borane/THF (63.3 ml of 1M solution) at 0° C. The mixture was boiled under reflux for 2 hours, cooled to 0° C., treated with water (10 ml) and then with 20% sodium hydroxide solution (10 ml). This mixture was boiled under reflux for 1 hour then concentrated under reduced pressure to approximately 20 ml, and water (50 ml) was added. The mixture was extracted with dichloromethane. The dichloromethane extracts were then extracted with dilute hydrochloric acid. The combined hydrochloric acid extracts were washed with dichloromethane, basified with 2M sodium hydroxide solution and then extracted with dichloromethane to give 2-[2-(N-benzyl-N-methylamino)ethoxy]-5-methoxybenzylamine as an oil not distilled.

EXAMPLE 28

O-Methylhydroxylamine hydrochloride (7.95 g) was added in portions to a solution of 2-[2-(N-benzyl-N-methylamino)ethoxy]-5-chlorobenzaldehyde (27.8 g) in pyridine (250 ml) and ethanol (250 ml). The mixture was boiled under reflux for 18 hours and then evaporated to dryness under reduced pressure. The residue was treated with sodium bicarbonate solution and extracted with dichloromethane to give a solid residue. The residue was triturated with petroleum ether b.p. 60°–80° C. (100 ml) and the mixture cooled in ice and then filtered to give 2-[2-(N-benzyl-N-methylamine)ethoxy]-5-chloro-O-methylbenzaldehyde oxime as a solid. This solid was dissolved in dry THF (100 ml) and borane/THF (250 ml, 1M solution) was added to the solution with stirring under nitrogen at 0° C. The mixture was boiled under reflux for 2 hours and then cooled to 0° C. Potassium hydroxide solution (80 ml, 10% w/w aqueous) was added dropwise to the mixture and the mixture was then boiled under reflux for 1 hour. The mixture was evaporated to near dryness under reduced pressure, diluted with water (200 ml) and extracted with dichloromethane. The combined dichloromethane extracts were extracted with 2M hydrochloric acid. The combined acidic extracts were washed with ethyl acetate and then basified with concentrated sodium hydroxide solution and then extracted with dichloromethane to give an oil. The oil was dissolved in ether, treated with charcoal and hot filtered. The filtrate was evaporated to give an oil which was distilled under vacuum to give 2-[2-(N-benzyl-N-methylamino)ethoxy]-5-chlorobenzylamine, b.p. 170° C. at 0.1 mbar.

EXAMPLE 29

Borane/THF (165 ml of a 1M solution) was added with stirring to a solution of 2-[3-(N-benzyl-N-methylamino) propoxy]-6-chlorobenzonitrile (13.01 g) in dry THF (100 ml) under nitrogen at ambient temperature. The mixture was boiled under reflux for 5 hours and then evaporated to dryness. The residue was heated on a steam bath under nitrogen for 2 hours, then cooled to ambient temperature. 1M Hydrochloric acid (100 ml) was added and the mixture was heated on a steam bath for 2 hours. The mixture was cooled in ice and basified with concentrated sodium hydroxide solution and then extracted with dichloromethane to give an oil. The oil was dissolved in ether and treated with ethereal hydrogen chloride to give a solid which was collected by filtration and recrystallised from propan-2-ol/IMS (2:1) to give 2-[3-(N-benzyl-N-methylamino)propoxy]-6-chlorobenzylamine dihydrochloride, m.p. 226°–228° C.

EXAMPLE 30

A mixture of 4-{N-[2-(4-chloro-2-dimethylaminomethylphenoxy) ethyl]-N-[methyl] aminomethyl}benzonitrile (10.16 g), powdered potassium hydroxide (20.0 g) and tert-butanol (100 ml) was boiled under reflux for 30 minutes. The mixture was cooled to ambient temperature and poured into saturated brine (300 ml). The mixture was extracted with dichloromethane to give an oil which was dissolved in hot acetonitrile and cooled to yield a precipitate which was collected by filtration and recrystallised from ethyl acetate/petroleum ether b.p. 60°–80° C., to give 4-{N-[2-(4-chloro-2-dimethylaminomethylphenoxy) ethyl]-N-[methyl] aminomethyl}benzamide, m.p. 108°–109° C.

EXAMPLE 31

A mixture of 4-{2-[N-(4-chlorobenzyl)-N-methylamino] ethoxy}-3-(dimethylaminomethyl)benzonitrile (5.0 g), tert-butanol (50 ml) and powdered potassium hydroxide (10.0 g) was boiled under reflux for 1 hour. The mixture was cooled to ambient temperature and poured into saturated brine (100 ml). The mixture was extracted with dichloromethane to give an oil which solidified slowly on drying under vacuum. The solid obtained was recrystallised from propan-2-ol to give 4-{2-[N-(4-chlorobenzyl)-N-methylamino]ethoxy}-3-(dimethylaminomethyl)benzamide, m.p. 123°–124° C.

EXAMPLE 32

A mixture of 2-[2-(N-benzyl-N-methylamino)ethoxy]-5-methoxy-N,N-dimethylbenzylamine (1.0 g), aqueous hydrobromic acid (10 ml, 48%) and hypophosphorous acid (0.05 ml, 50% by weight aqueous solution) was boiled under reflux under nitrogen for 1 hour. The mixture was evaporated to dryness under reduced pressure and the residue was neutralised with saturated sodium bicarbonate solution and then basified to pH 9 with 2M sodium hydroxide solution. The mixture was extracted with dichloromethane to give a gum. The gum was purified by flash column chromatography on silica using ethyl acetate/methanol/triethylamine (18:2:1) as the mobile phase to give an oil which was dissolved in ether and acidified with ethereal hydrogen chloride to give a solid which was collected by filtration and then recrystallised from propan-2-ol to give 4-[2-(N-benzyl-N-methylamino)ethoxy]-3-(dimethylaminomethyl)phenol dihydrochloride, m.p. 199°–200° C.

EXAMPLE 33

A mixture of 6-chloro-2-{2-[N-(2-methoxybenzyl)-N-methylamino]ethoxy}-N,N-dimethylbenzylamine (2.95 g), 48% aqueous hydrobromic acid (30 ml) and 50% aqueous hypophosphorous acid (0.15 ml) was boiled under reflux for 2 hours under nitrogen. The mixture was worked up as described in Example 32 but without chromatography to give an oil which was distilled under high vacuum to give an oil b.p. 190° C. at 0.06 mbar which was treated with ethereal hydrogen chloride and filtered to give 2-{N-[2-(3-chloro-2-dimethylaminomethylphenoxy)ethyl]-N-[methyl]aminomethyl}phenol dihydrochloride, m.p. 130° C.

EXAMPLE 34

2-[2-(N-Benzyl-N-methylamino)ethoxy]-5-methoxybenzylamine (16.8 g) was added dropwise to cold formic acid (20 ml) and the mixture was treated with formaldehyde (20 ml of a 38% aqueous solution). The mixture was heated on a steam bath for 3 hours, then cooled and evaporated to dryness under reduced pressure. The residue was dissolved in dilute hydrochloric acid and washed with dichloromethane. The acidic layer was basified with 2M sodium hydroxide solution and then extracted with dichloromethane to give an oil which was triturated with ether and then filtered. The filtrate was evaporated to give an oil which was dissolved in ether and acidified with ethereal hydrogen chloride to give a solid which was collected by filtration. The solid was triturated with ether to leave a sticky solid which was left standing exposed to the atmosphere over 5 days to give 2-[2-(N-benzyl-N-methylamino)ethoxy]5-methoxy-N,N-dimethylbenzylamine dihydrochloride, (0.3 $H_2O$) m.p. 219°–221° C.

EXAMPLE 35

2-[3-(N-Benzyl-N-methylamino)propoxy]-6-chlorobenzylamine (6.0 g) was added in portions to 98% formic acid (6 ml) at 0° C. with stirring. Formaldehyde (6 ml of a 37% aqueous solution) was added and the mixture was heated on a steam bath for 3 hours. The mixture was evaporated to dryness under reduced pressure and the residue was treated with 2M hydrochloric acid (50 ml), washed with ethyl acetate, and basified with concentrated sodium hydroxide solution. The mixture was extracted with dichloromethane to give a residue which was distilled under vacuum to give an oil, b.p. 150° C. at 0.06 mbar. This oil was dissolved in ether and treated with ethereal hydrogen chloride and the precipitate was collected by filtration and recrystallised from propan-2-ol to give a solid which was dried under vacuum at 75° C. for 48 hours to give 2-[3-(N-benzyl-N-methylamino)propoxy]-6-chloro-N,N-dimethylbenzylamine dihydrochloride hemihydrate, m.p. 161°–164° C.

EXAMPLE 36

A solution of borane/THF (27 ml, 1M solution) was added to a solution of N-(4-chloro-α,α-dimethylbenzyl)-2-(2-dimethylcarbamoylphenoxy)acetamide (2.0 g) in THF (20 ml) at 0° C. with stirring under a nitrogen atmosphere. The mixture was warmed to ambient temperature and then boiled under reflux for 1 hour. The mixture was evaporated to dryness and 2M hydrochloric acid (50 ml) was added carefully. The mixture was heated on a steam bath for 2 hours, then cooled, washed with ethyl acetate, basified with 2M sodium hydroxide solution and extracted into dichloromethane to give an oil which was distilled under high vacuum to give an oil, b.p. 150° C. at 0.13 mbar. The oil was dissolved in ether and acidified with ethereal hydrogen chloride. The precipitate was collected by filtration to give 2-[2-(4-chloro-α,α-dimethylbenzylamino) ethoxy]-N,N-dimethylbenzylamine dihydrochloride hemihydrate m.p. 140° C. (with effervescence).

EXAMPLE 37

A solution of borane/THF (80 ml, 1M solution) was added to a solution of 2-[2-(N-benzyl-N-methylamino) ethoxy]-6-chlorobenzonitrile (6.02 g) in THF (60 ml) at ambient temperature under nitrogen with stirring. The mixture was stirred at ambient temperature for 4 hours and then boiled under reflux for 1 hour. The mixture was evaporated to dryness and the residue was heated on a steam bath under nitrogen for 1 hour and then 1M hydrochloric acid (100 ml) was added and the mixture was heated for a further 2 hours. The mixture was cooled, washed with ethyl acetate, basified with concentrated sodium hydroxide solution and extracted with dichloromethane to give an oil. The oil was dissolved in ether and treated with ethereal hydrogen chloride to give a solid which was collected by filtration. The solid was stirred with 2M sodium hydroxide solution and then extracted with dichloromethane to give an oil which was distilled under vacuum. The oil which boiled at 140° C. at 0.04 mbar was dissolved in ether and treated with ethereal hydrogen chloride. The precipitated solid was collected by filtration and dried to give 2-[2-(N-benzyl-N-methylamino) ethoxy]-6-chlorobenzylamine, m.p. 85° C.

EXAMPLE 38 a) A solution of N-benzyl-N-methylethanolamine (13.4 g) in dry DMF (30 ml) was added dropwise with stirring to a suspension of sodium hydride (4.75 g, 60% dispersion in mineral oil) in DMF (60 ml) at ambient temperature under nitrogen over 20 minutes. The mixture was stirred and heated at 50° C. for 1 hour until the evolution of hydrogen ceased. The mixture was cooled at ambient temperature and a solution of 2-chloro-6-fluorobenzaldehyde (15.8 g) in DMF (15 ml) was added over 30 minutes. The mixture was heated at 70° C. for 2 hours and then cooled and poured onto ice/water (1 l). The mixture was extracted with ethyl acetate. The combined ethyl acetate extracts were washed with 2M sodium hydroxide solution and then brine, dried and evaporated to give 2-[2-(N-benzyl-N-methylamino)ethoxy]-6-chlorobenzaldehyde as an oil.

b) A mixture of the product from a) (27.64 g), absolute ethanol (270 ml), pyridine (270 ml) and O-methylhydroxylamine hydrochloride (7.95 g) was boiled under reflux for 16 hours. The mixture was evaporated to dryness under reduced pressure and then further dried by azeotropic distillation with toluene to give an oil. The oil was washed with petroleum ether, b.p. 40°–60° C. The residue was partitioned between saturated sodium bicarbonate solution and dichloromethane. The organic layer was separated, dried and evaporated to give an oil which was dried by azeotropic distillation with toluene to give 2-[2-(N-benzyl-N-methylamino)ethoxy]-6-chloro-O-methylbenzaldehyde oxime as an oil.

c) Borane/THF (205 ml, of a 1M solution) was added to a solution of the product from b) (17.0 g) in THF (200 ml) at 0°–5° C. under nitrogen over 20 minutes. The mixture was warmed to ambient temperature and then boiled under reflux for 2 hours. The mixture was cooled to 0° C. and treated dropwise with water (40 ml) and then 20% potassium hydroxide solution (40 ml). The mixture was boiled under reflux for 1 hour and then evaporated to reduce the volume to approximately 100 ml. Water (200 ml) was added and the mixture was extracted with dichloromethane. The combined dichloromethane extracts were extracted with 2M hydrochloric acid and the combined acidic extracts were washed with dichloromethane, basified with 2M sodium hydroxide solution and back extracted with dichloromethane to give 2-[2-(N-benzyl-N-methylamino)ethoxy]-6-chlorobenzylamine as an oil.

d) The product from c) (8.71 g) was added to cold formic acid (10 ml). Aqueous formaldehyde (10 ml, of a 48% solution) was added and the mixture was boiled under reflux for 3 hours. The mixture was evaporated to near dryness and dilute hydrochloric acid (50 ml) was added. The mixture was washed with dichloromethane and then the aqueous layer was basified with 2M sodium hydroxide solution and extracted with dichloromethane to give an oil. The oil was distilled under high vacuum to give 2-[2-(N-benzyl-N-methylamino)ethoxy]-6-chloro-N,N-dimethyl benzylamine as an oil, b.p. 150° C. at 0.06 mbar. The oil was dissolved in ether and acidified with ethereal hydrogen chloride. The solid which precipitated was collected by filtration, dried and recrystallised from propan-2-ol to give 2-[2-(N-benzyl-N-methylamino)ethoxy]-6-chloro-N,N-dimethylbenzylamine dihydrochloride, m.p. 232°–233° C.

EXAMPLE 39 a) A solution of N-benzyl-N-methylethanolamine (145 g) in dry DMF (500 ml) was added dropwise to a stirred suspension of sodium hydride (35.15 g of a 60% dispersion in mineral oil) in dry DMF (1000 ml) over 20 minutes under nitrogen. The mixture was heated on a steam bath for 30 minutes to give a solution. The solution was cooled to ambient temperature and a solution of 2-chloro-6-fluorobenzonitrile (136.7 g) in dry DMF (300 ml) was added over 30 minutes with stirring. The mixture was heated on a steam bath for 3 hours with stirring and distilled at approximately 13 mbar to remove 1 liter of DMF. The residue was cooled to ambient temperature and poured into ice (2 l), basified with 5M sodium hydroxide solution to pH 14 and extracted with dichloromethane to give an oil. This oil was dissolved in ether (2 l) and washed with water (4×200 ml). The ether solution was extracted with 2M hydrochloric acid (500 ml) which gave three layers in the separating funnel. The bottom two layers were run off and the top ether layer was extracted with 2M hydrochloric acid (2×250 ml). The combined acidic layers were basified with concentrated sodium hydroxide solution with cooling and then extracted with dichloromethane to give 2-[2-(N-benzyl-N-methylamino)ethoxy]-6-chlorobenzonitrile as an oil.

b) A solution of lithium aluminium hydride in THF (790 ml of a 1M solution) was stirred under nitrogen at ambient temperature and diluted with dry THF (1 l) and then a solution of 2-[2-(N-benzyl-N-methylamino)ethoxy]-6- chlorobenzonitrile (237 g) in dry THF (200 ml) was added over 30 minutes. When approximately three-quarters of the solution had been added an exotherm was observed and this was checked by cooling the reaction mixture in an ice/water bath. The mixture was stirred for 1 hour after the addition and then quenched by the cautious addition of water (30 ml), 15% sodium hydroxide solution (30 ml) and water (90 ml). The mixture was diluted with ethyl acetate (1 l) and filtered through a filter aid. The filter aid was boiled with ethyl acetate (2×500 ml) and filtered through a filter aid. The combined filtrates were dried and evaporated to give 2-[2-(N-benzyl-N-methylamino)ethoxy]-6-chlorobenzylamine as an oil.

c) 2-[2-(N-Benzyl-N-methylamino)ethoxy]-6-chlorobenzylamine (222.6 g) was added dropwise to ice cool 98% formic acid (225 ml) with stirring. Aqueous formaldehyde (225 ml of a 37–40% aqueous solution) was added and the mixture warmed to 60° C. in a water bath. The mixture was then heated on a steam bath for 1 hour and then evaporated to dryness. The residue was dissolved in dilute hydrochloric acid (300 ml) and washed with dichloromethane. The aqueous layer was basified with 5M sodium hydroxide solution and extracted with dichloromethane to give 2-[2-(N-benzyl-N-methylamino)ethoxy]-6-chloro-N,N-methylbenzylamine which was poured into cooled dilute hydrochloric acid (50% by volume). The solution was washed with dichloromethane and the aqueous layer evaporated to dryness to give 2-[2-(N-benzyl-N-ethylamino)ethoxy]-6-chloro-N-N-dimethylbenzylamine dihydrochloride, m.p. 238°–239° C.

PREPARATION OF STARTING MATERIALS

2-[3-(N-Benzyl-N-methylamino)propoxy]-6-chlorobenzonitrile

A solution of N-benzyl-N-methylpropanolamine (10.0 g) in dry DMF (50 ml) was added dropwise to a stirred suspension of sodium hydride (2.24 g, 60% dispersion in mineral oil) in dry DMF (40 ml) under nitrogen at approximately 40° C. The mixture was stirred at this temperature for 2 hours and then cooled to ambient temperature and then a solution of 2-chloro-6-fluorobenzonitrile (8.68 g) in dry DMF (50 ml) was added dropwise and the mixture heated on a steam bath for 5 hours. The mixture was left standing at ambient temperature for 16 hours and then poured onto ice/water (500 ml), acidified with concentrated hydrochloric acid, washed with ethyl acetate, basified with concentrated sodium hydroxide solution and then extracted with dichloromethane to give 2-[3-(N-benzyl-N-methylamino)propoxy]-6-chlorobenzonitrile as an oil.

N-(4-Chloro-α,α-dimethylbenzyl)-2-(2-dimethylcarbamoylphenoxy)acetamide

A mixture of the 2-hydroxy-N,N-dimethylbenzamide (0.68 g) in DMSO (5 ml) was added to a stirred suspension of sodium hydride (163 mg of a 60% dispersion in mineral oil) in DMSO (5 ml) at ambient temperature over 5 minutes with stirring. The mixture was stirred until the evolution of hydrogen ceased and then a solution of 2-chloro-N-[1-(4-chlorophenyl)-1-methylethyl]-acetamide (prepared by reacting α,α-dimethylbenzylamine with chloroacetyl chloride) (1.0 g) in DMSO (5 ml) was added dropwise over 5 minutes with stirring. The mixture was stirred at ambient temperature for 16 hours and then poured into ice water (200 ml) and extracted with ethyl acetate to give a solid which was recrystallised from ethyl acetate/petroleum ether, b.p. 60°–80° C. to give N-(4-chloro-α,α-dimethylbenzyl)-2-(2-dimethylcarbamoyl-phenoxy)acetamide, m.p. 127°–9° C.

2-Hydroxy-1-(dimethylaminomethyl)naphthalene

A mixture of 2-hydroxynaphthalene (20.18 g), N,N,N',N'-tetramethyldiaminomethane (19.10 ml) and 1,4-dioxane (200 ml) was heated on a steam bath for 24 hours and then evaporated to dryness under reduced pressure. The residue was dissolved in 2M hydrochloric acid and washed with ethyl acetate, neutralised with concentrated sodium hydroxide solution and extracted with dichloromethane to give a solid which was recrystallised from petroleum ether, b.p. 60°–80° C. to give 2-hydroxy-1-(dimethylaminomethyl)naphthalene, m.p. 79°–80° C.

4-Chloro-2-(dimethylaminomethyl)phenol

A solution of 4-chlorophenol (25.72 g), N,N,N',N'-tetramethyldiaminomethane (27.2 ml) and 1,4-dioxane (250 ml) was heated on a steam bath for 16 hours. The mixture was evaporated to dryness and the residue was dissolved in 2M hydrochloric acid, washed with dichloromethane, basified with concentrated sodium hydroxide solution and extracted with dichloromethane to give an oil which was distilled to give 4-chloro-2-(dimethylaminomethyl)phenol, b.p. 90°–97° C. at 0.26 mbar.

The following were prepared in a similar manner:

1) 4-fluoro-2-(dimethylaminomethyl)phenol b.p. 70° C. at 0.1 mbar, from 4-fluorophenol;

2) methyl 4-hydroxy-3-((dimethylaminomethyl)benzoate as a solid, from methyl 4-hydroxybenzoate (without the final distillation);

3) 2-chloro-6-(dimethylaminomethyl)phenol from 2-chlorophenol;

4) 4-hydroxy-3-(dimethylaminomethyl)benzonitrile as an oil (without the final distillation), from 4-hydroxybenzonitrile;

5) 3-chloro-2-((dimethylaminomethyl)phenol (first fraction after flash column chromatography of the products on silica using ethyl acetate/petroleum ether b.p. 60°–80° C. as the mobile phase, identified by $^1$H NMR spectroscopy) and 5-chloro-2-(dimethylaminomethyl)phenol (second product fraction) from 3-chlorophenol and 6) 2-(dimethylaminomethyl)-4-(trifluoromethyl)phenol from 4-(trifluoromethyl)phenol.

3,4-Dichloro-2-(dimethylaminomethyl)phenol and 4,5-Dichloro-2-(dimethylaminomethyl)phenol A mixture of 3,4-dichlorophenyl (20.38 g) and N,N,N',N'-tetramethyldiaminomethane (17.0 ml) and 1,4-dioxane (200 ml) was heated on a steam bath for 48 hours. The mixture was worked up as described in the previous experiment to give an oil which was purified by flash column chromatography on silica using ethyl acetate/triethylamine, (9:1) as the mobile phase. The first product fraction was recrystallised from petroleum ether b.p. 40°–60° C. and was identified $^1$H NMR spectroscopy as 3,4-dichloro-2-(dimethylaminomethyl)phenol m.p. 77°–79° C. The second product fraction was identified as 4,5-dichloro-2-(dimethylaminomethyl)phenol as an oil.

4-Chloro-2-(piperidinomethyl)phenol

A mixture of 4-chlorophenol (12.86 g), absolute ethanol (30 ml), formaldehyde (7.49 ml of a 37% aqueous solution)

and piperidine (10.88 ml) was boiled under reflux for 4 hours. The mixture was evaporated to dryness and toluene (50 ml) was added. The mixture was evaporated to dryness and the residue was dissolved in 2M hydrochloric acid, washed with ethyl acetate, basified with concentrated sodium hydroxide solution and then extracted with dichloromethane to give 4-chloro-2-(piperidinomethyl)phenol as an oil which solidified on standing, m.p. 53°–56° C.

2-Dimethylaminomethyl-3-hydroxybenzonitrile

A mixture of 3-hydroxybenzonitrile (20.0 g) and N,N,N', N'-tetramethyldiaminomethane (22.9 ml) in 1,4-dioxane (200 ml) was heated on a steam bath for 48 hours. The mixture was evaporated to dryness and the residue dissolved in 2M hydrochloric acid. The solution was washed with ethyl acetate and then the acidic layer was basified with concentrated sodium hydroxide solution and extracted with dichloromethane to give an oil which was purified by column chromatography on silica to give 2-dimethylaminomethyl-3-hydroxybenzonitrile. The structure was confirmed by $^1$H NMR spectroscopy.

2-Dimethylaminomethyl-3-methoxyphenol and 2-dimethylaminomethyl-5-methoxyphenol A mixture of 3-methoxyphenol (20.0 g), N,N,N',N'-tetramethyldiaminomethane (22.0 ml) and 1,4-dioxane (200 ml) was heated on a steam bath for 24 hours. The mixture was evaporated to dryness and then extracted with 2M hydrochloric acid. The acidic extracts were washed with ethyl acetate and basified with concentrated sodium hydroxide solution and extracted with dichloromethane to give a mixture of 2-dimethylaminomethyl-3-methoxyphenol and 2-dimethylaminomethyl-5-methoxyphenol as an oil.

2-[2-(N-Benzyl-N-methylamino)ethoxy]-5-chlorobenzaldehyde

A solution of 5-chloro-2-hydroxybenzaldehyde (25.68 g) in dry DMF (100 ml) was added dropwise to a stirred suspension of sodium hydride (6.84 g of a 60% dispersion in mineral oil) in dry DMF (100 ml) at ambient temperature under nitrogen with stirring. The mixture was heated on a steam bath for 1.5 hours, then cooled to ambient temperature and a solution of N-benzyl-2-chloro-N-methylethylamine in toluene (60 ml) [prepared by dissolving the hydrochloride (48.5 g) in 2M sodium hydroxide solution (50 ml) and extracting with toluene (2×30 ml) with drying] and the resulting mixture was heated on a steam bath for 4 hours. The mixture was cooled to ambient temperature and then poured into ice/water (100 ml). The mixture was extracted with ether and the combined ether extracts were washed with 2M sodium hydroxide solution until the washes were colourless. The ether extracts were then washed with 2M hydrochloric acid. The acidic extracts were basified with concentrated sodium hydroxide solution and extracted with dichloromethane to give an oil. A portion of the oil was dissolved in ether and treated with ethereal hydrogen chloride. The solid which precipitated was collected by filtration and recrystallised from propan-2-ol to give 2-[2-(N-benzyl-N-methylamino)ethoxy]-5-chlorobenzaldehyde, m.p. 154°–155° C.

2-[2-(N-Benzyl-N-methylamino)ethoxy]-5-methoxybenzaldehyde hydrochloride

In a similar manner to the previous example, a solution of 2-hydroxy-5-methoxybenzaldehyde (25.0 g) in DMF (50 ml) was added to a stirred suspension of sodium hydride (6.84 g of a 60% dispersion in mineral oil) in dry DMF (125 ml) at ambient temperature under nitrogen with stirring. The mixture was heated at 70° C. for 2 hours and then cooled to ambient temperature and a solution of N-benzyl-2-chloro-N-methylethylamine in toluene (75 ml) was added [prepared from 48.5 g of the hydrochloride salt]. The oil obtained after work up was distilled under vacuum to give 2-[2-(N-benzyl-N-methylamino)ethoxy]-5-methoxybenzaldehyde as an oil. A sample of this oil which boiled at 202°–206° C. at 0.65 mbar was dissolved in ether and acidified with ethereal hydrogen chloride. The precipitate was collected by filtration, washed with ether to give 2-[2-(N-benzyl-N-methylamino)ethoxy]-5-methoxybenzaldehyde hydrochloride, m.p. 167°–169° C.

N-(4-Chlorobenzyl)-N-methylethanolamine

A mixture of N-methylethanolamine (21.2 g), 4-chlorobenzyl chloride (35.0 g) and xylene (100 ml) was stirred and boiled under reflux for 7 hours. The mixture was allowed to cool to ambient temperature and the solid mass was dissolved in 2M hydrochloric acid. The aqueous phase was separated off, washed with ether, basified with 2M sodium hydroxide solution and extracted with dichloromethane to give an oil which was distilled at 120°–125° C. at 0.3 mbar to give N-(4-chlorobenzyl)-N-methylethanolamine.

4-[N-(2-Hydroxyethyl)-N-methylaminomethyl]benzonitrile

A mixture of 4-bromomethylbenzonitrile (49.7 g), N-methylethanolamine (19.0 g) and xylene (100 ml) was boiled under reflux with stirring for 7 hours and then worked up as described in the previous example to give an oil which was distilled at 142°–146° C. at 0.5 mbar to give 4-[N-(2-hydroxyethyl)-N-methylaminomethyl]benzonitrile as an oil.

N-(2-Chlorobenzyl)-N-methylethanolamine

N-(2-Chlorobenzyl)-N-methylethanolamine was prepared in a similar manner to the two previous examples by reacting 2-chlorobenzyl chloride with N-methylethanolamine in xylene.

2-{2-[N-(2-Methoxybenzyl)-N-methylamino]ethoxy}-6-chloro-N,N-dimethylbenzylamine 2-Methoxybenzyl bromide [J.Med. Chem., 32, 1761 (1989)] was reacted with N-methylethanolamine as described in the three previous examples to give N-(2-methoxybenzyl)-N-methylethanolamine which was reacted with 3-chloro-2-(dimethylaminomethyl)phenol in a similar manner to Example 1 (except that conversion into the dihydrochloride salt was omitted) to give the title compound b.p. 100° C. at 0.01 mbar.

N-Benzyl-2-chloro-N-methylethylamine hydrochloride

N-Benzyl-N-methylethanolamine (200 ml) was dissolved in chloroform (600 ml). The solution was cooled to 0° C. with stirring and then thionyl chloride (100 ml) was added dropwise, with stirring, at a rate such that the temperature of the reaction mixture was kept below 15° C. The mixture was boiled under reflux for 2 hours and then evaporated to dryness. The solid residue was triturated with ether, filtered and dried to give N-benzyl-2-chloro-N-methylethylamine hydrochloride.

4-{2-[N-(4-chlorobenzyl)-N-methylamino]ethoxy}-3-(dimethylaminomethyl)benzonitrile The title compound (b.p. 100° C. at 0.1 mbar) was prepared by reacting 4-hydroxy-3-(dimethylaminomethyl) benzonitrile (7.32 g) with N-(4-chlorobenzyl)-N-methylethanolamine (8.29 g) in a similar manner to Example 4.

PHARMACEUTICAL EXAMPLES

Example U

In the preparation of capsules, 10 parts by weight of active compound and 240 parts by weight of lactose are de-aggregated and blended. The mixture is filled into hard gelatin capsules, each capsule containing 10 mg active compound.

Example V

Tablets are prepared from the following ingredients.

|  | Parts by Weight |
| --- | --- |
| Active compound | 10 |
| Lactose | 190 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinylpyrrolidone in ethanol. The dry granulate is blended with magnesium stearate and the rest of the starch. The mixture is then compressed in a tableting machine to give tablets containing 10 mg of active compound.

Example W

Tablets are prepared by the method of the previous Example. The tablets are enteric coated in a conventional manner using a solution of 20% cellulose acetate phthalate and 3% diethyl phthalate in ethanol:dichloromethane (1:1).

Example X

In the preparation of suppositories, 100 parts by weight of active compound is incorporated in 1300 parts by weight of semi-synthetic glycerides as the suppository base and the mixture formed into suppositories each containing 100 mg of active ingredient.

Example Y

In the preparation of capsules, 50 parts by weight of active compound, 300 parts by weight of lactose and 3 parts by weight of magnesium stearate are de-aggregated and blended. The mixture is filled into hard gelatin capsules, each capsule containing 50 mg of active ingredient.

Example Z

The active compound is incorporated into the base by thorough homogenization until the drug is evenly distributed. The ointment is packed into 10 g amber jars with screw-capped lined lids.

Active compound 0.1 g
White soft paraffin to 10 g

We claim:
1. Compounds of formula I

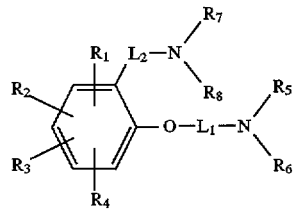

including pharmaceutically acceptable salts thereof in which $R_1$, $R_2$, $R_3$, and $R_4$ independently represent hydrogen, hydroxy, halo, a halogenated $C_{1-4}$ alkyl group, a halogenated $C_{1-4}$ alkoxy group, a $C_{1-6}$ alkyl group, a $C_{1-6}$ alkoxy group, cyano, a carbamoyl group of formula $CONR_AR_B$ (in which $R_A$ and $R_B$ independently represent hydrogen or a $C_{1-4}$ alkyl group), a ($C_{1-6}$ alkoxy) carbonyl group, or $R_1$ and $R_2$ together with the phenyl ring to which they are attached represent a naphthalene ring which is optionally substituted by one or more of the following: a $C_{1-6}$ alkyl group, a $C_{1-6}$ alkoxy group or halo;

$L_1$ represents a $C_{2-6}$ alkylene chain optionally substituted by one or more $C_{1-4}$ alkyl groups;

$R_5$ represents hydrogen or a $C_{1-6}$ alkyl group;

$R_6$ represents hydrogen or a $C_{1-6}$ alkyl group, a phenyl $C_{1-6}$ alkyl chain (in which the alkyl chain is optionally substituted by one or more $C_{1-6}$ alkyl groups and the phenyl ring is optionally substituted by one or more of the following: a $C_{1-6}$ alkyl group, a $C_{1-6}$ alkoxy group, halo, hydroxy, cyano or a carbamoyl group of formula $CONR_cR_d$ in which $R_c$ and $R_d$ independently represent hydrogen or a $C_{1-4}$ alkyl group), or $R_5$ and $R_6$ together with the nitrogen atom to which they are attached represent a saturated 3–7 membered heterocyclic ring, optionally containing sulphur, oxygen or an additional nitrogen atom, wherein the ring is optionally substituted by one or more $C_{1-4}$ alkyl groups;

$L_2$ represents a $C_{1-6}$ alkylene chain optionally substituted by one or more $C_{1-4}$ alkyl groups; and $R_7$ and $R_8$ independently represent hydrogen or a $C_{1-6}$ alkyl group or $R_7$ and $R_8$ together with the nitrogen atom to which they are attached represent a saturated 3–7 membered heterocyclic ring, optionally containing sulphur, oxygen or an additional nitrogen atom, wherein the ring is optionally substituted by one or more $C_{1-4}$ alkyl groups;

excluding the following compounds:

1) 2-(4-aminobutoxy)-N,N-dimethylbenzylamine;
2) N-isopropyl-2-[2-(isopropylamino)ethoxy]-α-methylbenzylamine; and
3) α-methyl-N-propyl-2-[2-(propylamino)ethoxy]benzylamine;

and with the proviso that, when a) $R_1$, $R_2$ and $R_3$ each represent hydrogen and $R_4$ is hydrogen or alkoxy
b) $L_1$ represents a $C_{2-6}$ alkylene chain
c) the group $NR_5R_6$ is amino, alkylamino, dialkylamino or a nitrogen containing heterocyclic group and
d) $L_2$ represents methylene then the group $NR_7R_8$ does not represent amino, alkylamino or piperidino.

2. Compounds according to claim 1 represented by formula II

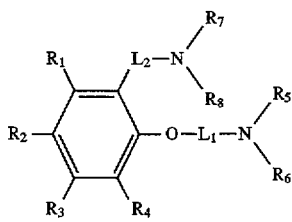

including pharmaceutically acceptable salts thereof in which
- $R_1$, $R_2$, $R_3$ and $R_4$ independently represent hydrogen, hydroxy, halo, a polyhalo $C_{1-4}$ alkyl group, a $C_{1-6}$ alkyl group, a $C_{1-6}$ alkoxy group, cyano, carbamoyl, a ($C_{1-6}$ alkoxy)carbonyl group, or $R_1$ and $R_2$ together with the phenyl ring to which they are attached represent a naphthalene ring;
- $L_1$ represents $C_{2-4}$ alkylene chain optionally substituted by one or more $C_{1-4}$ alkyl groups;
- $R_5$ represents hydrogen or a $C_{1-6}$ alkyl group;
- $R_6$ represents a $C_{1-6}$ alkyl group, a phenyl $C_{1-6}$ alkyl chain; or $R_5$ and $R_6$ together with the nitrogen atom to which they are attached represent a pyrrolidine ring, a piperidine ring, a morpholine ring, a thiamorpholine ring, an azepine ring or an N-methylpiperazine ring;
- $L_2$ represents a $C_{1-4}$ alkylene chain optionally substituted by one or more $C_{1-4}$ alkyl groups; and
- $R_7$ and $R_8$ independently represent hydrogen or a $C_{1-6}$ alkyl group, or $R_7$ and $R_8$ together with the nitrogen atom to which they are attached represent a pyrrolidine ring, a piperidine ring, a morpholine ring, a thiamorpholine ring, an azepine ring or an N-methylpiperazine ring.

3. Compounds according to claim 2 in which
$R_1$ represents hydrogen, halo or cyano;
$R_2$ represents hydrogen, halo, a perfluoro$C_{1-4}$ alkyl group, hydroxy, cyano, carbamoyl, a $C_{1-4}$ alkoxy group or a ($C_{1-4}$ alkoxy)carbonyl group; or
$R_1$ and $R_2$ together with the phenyl ring to which they are attached represent a naphthalene ring;
$R_3$ represents hydrogen, halo or a $C_{1-4}$ alkoxy group; and
$R_4$ represents hydrogen or halo.

4. Compounds according to claim 2 in which $L_2$ represents a $C_{1-3}$ alkylene chain optionally substituted by one or more $C_{1-4}$ alkyl groups.

5. Compounds according to claim 2 in which $R_5$ represents hydrogen or a $C_{1-4}$ alkyl group; and $R_6$ represents a $C_{1-4}$ alkyl group, or a phenyl $C_{1-4}$ alkyl chain in which the phenyl ring is optionally substituted by one or more of the following: halo, hydroxy, cyano or carbamoyl; or $R_5$ and $R_6$ together with the nitrogen atom to which they are attached represent a piperidine ring.

6. Compounds according to claim 2 in which $R_7$ and $R_8$ independently represent hydrogen or a $C_{1-4}$ alkyl group; or $R_7$ and $R_8$ together with the nitrogen atom to which they are attached represent a piperidine ring.

7. Compounds according to claim 2 in which one of $R_1$, $R_2$, $R_3$ and $R_4$ represents halo and the others represent hydrogen; $L_1$ represents ethylene or trimethylene; $R_5$ represents methyl; $R_6$ represents benzyl (optionally substituted by halo or hydroxy); $L_2$ represents methylene; and $R_7$ and $R_8$ both represent methyl.

8. A compound according to claim 1 selected from:

2-[2-(N-benzyl-N-methylamino)ethoxy]-5-fluoro-N,N-dimethylbenzylamine;
2-[2-(N-benzyl-N-methylamino)ethoxy]-4-chloro-N,N-dimethylbenzylamine;
N-benzyl-2-[1-(dimethylaminomethyl)naphth-2-yloxy]-N-methylethylamine;
N-benzyl-2-[4-chloro-2-(piperidinomethyl)phenoxy]-N-methylethylamine;
2-[3-(N-benzyl-N-methylamino)propoxy]-5-chloro-N,N-dimethylbenzylamine;
2-[2-(N-benzyl-N-methylamino)ethoxy]-5,6-dichloro-N,N-dimethylbenzylamine;
2-[2-(N-benzyl-N-methylamino)ethoxy]-N,N-dimethylbenzylamine; and
5-chloro-2-(2-dimethylaminoethoxy)-N,N-dimethylbenzylamine.

9. A compound according to claim 1 selected from:
2-[2-(N-benzyl-N-methylamino)ethoxy]-6-chloro-N,N-dimethylbenzylamine;
2-{2-[N-(2-chlorobenzyl)-N-methylamino]ethoxy}-N,N-dimethylbenzylamine;
2-{[N-(4-chlorobenzyl)-N-methylamino]ethoxy}-N,N-dimethylbenzylamine;
2-[2-N-benzyl-N-methylamino)ethoxy]-5-chloro-N,N-dimethylbenzylamine;
2-[3-(N-benzyl-N-methylamino)propoxy]-6-chloro-N,N-dimethylbenzylamine;
2-[2-(4-chloro-α,α-dimethylbenzylamino)ethoxy]-N,N-dimethylbenzylamine;
2-[2-(N-benzyl-N-methylamino)ethoxy]-6-chlorobenzylamine; and
2-{N-[2-(3-chloro-2-dimethylaminomethylphenoxy)ethyl]-N-methylaminomethyl}phenol.

10. A pharmaceutical composition comprising a therapeutically effective amount of a compound of formula I

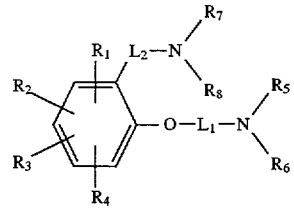

including pharmaceutically acceptable salts thereof in which $R_1$, $R_2$, $R_3$, and $R_4$ independently represent hydrogen, hydroxy, halo, a halogenated $C_{1-4}$ alkyl group, a halogenated $C_{1-4}$ alkoxy group, a $C_{1-6}$ alkyl group, a $C_{1-6}$ alkoxy group, cyano, a carbamoyl group of formula $CONR_AR_B$ (in which $R_A$ and $R_B$ independently represent hydrogen or a $C_{1-4}$ alkyl group), a ($C_{1-6}$ alkoxy)carbonyl group, or $R_1$ and $R_2$ together with the phenyl ring to which they are attached represent a naphthalene ring which is optionally substituted by one or more of the following: a $C_{1-6}$ alkyl group, a $C_{1-6}$ alkoxy group or halo;

$L_1$ represents a $C_{2-6}$ alkylene chain optionally substituted by one or more $C_{1-4}$ alkyl groups;

$R_5$ represents hydrogen or a $C_{1-6}$ alkyl group;

$R_6$ represents hydrogen or a $C_{1-6}$ alkyl group, a phenyl $C_{1-6}$ alkyl chain (in which the alkyl chain is optionally substituted by one or more $C_{1-6}$ alkyl groups and the phenyl ring is optionally substituted by one or more of the following: a $C_{1-6}$ alkyl group, a $C_{1-6}$ alkoxy group, halo, hydroxy, cyano or a carbamoyl group of formula $CONR_cR_d$ in which $R_c$ and $R_d$ independently represent hydrogen or a $C_{1-4}$ alkyl group), or $R_5$ and $R_6$ together with the nitrogen atom to which they are attached represent a saturated 3–7 membered heterocyclic ring, optionally containing sulphur, oxygen or an additional nitrogen atom, wherein the ring is optionally substituted by one or more $C_{1-4}$ alkyl groups;

$L_2$ represents a $C_{1-6}$ alkylene chain optionally substituted by one or more $C_{1-4}$ alkyl groups;

$R_7$ and $R_8$ independently represent hydrogen or a $C_{1-6}$ alkyl group or $R_7$ and $R_8$ together with the nitrogen atom to which they are attached represent a saturated 3–7 membered heterocyclic ring, optionally containing sulphur, oxygen or an additional nitrogen atom, wherein the ring is optionally substituted by one or more $C_{1-4}$ alkyl groups; together with a pharmaceutically acceptable diluent or carrier.

11. A method of treating conditions associated with inflammation, allergy, rheumatism, neurological damage or the immune system comprising the administration of a therapeutically or prophylactically effective amount of a compound of formula I, as defined in claim 10, to a mammal in need thereof.

12. A process to prepare compounds of formula I as claimed in claim 1 comprising a) reacting a compound of formula IV

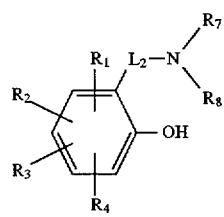

in which $R_1$, $R_2$, $R_3$, $R_4$, $R_7$, $R_8$ and $L_2$ are as previously defined, with a compound formula V

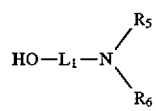

in which $R_5$, $R_6$ and $L_1$ are as previously defined, in the presence of a dialkyl azodicarboxylate and a phosphorus (III) reagent in the presence of an inert organic liquid at a temperature in the range from 0° C. up to the boiling point of the inert organic liquid; or b) reacting a compound of formula IV with a compound of formula VI

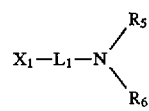

in which $R_5$, $R_6$ and $L_1$ are as previously defined and $X_1$ represents a leaving group, in the presence of a base, in the presence of an inert organic liquid at a temperature in the range from 0° C. up to the boiling point of the inert organic liquid; or c) reacting a compound of formula VII

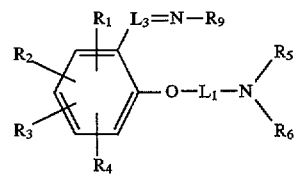

in which $R_1$, $R_2$, $R_3$, $R_4$, $R_5$, $R_6$ and $L_1$ are as previously defined and —$L_3$=N—$R_9$ represents a group which on reductive cleavage gives —$L_2$—$NH_2$, with a reducing agent, in an inert organic liquid at a temperature in the range from 0° C. up to the boiling point of the inert organic liquid, to give compounds of formula I in which $R_7$ and $R_8$ represent hydrogen; or d) reacting a compound of formula VIII

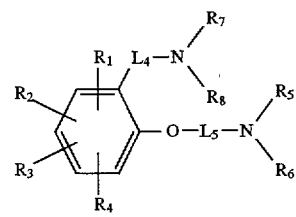

in which $R_1$, $R_2$, $R_3$, $R_4$, $R_5$, $R_6$, $R_7$ and $R_8$ are as previously defined and $L_4$ represents a group which on reduction gives $L_2$, and $L_5$ represents a group which on reduction gives $L_1$, with a reducing agent, in an inert organic liquid at a temperature in the range from 0° C. up to the boiling point of the inert organic liquid; or e) reacting a compound of formula IX

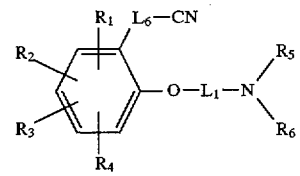

in which $R_1$, $R_2$, $R_3$, $R_4$, $R_5$, $R_6$ and $L_1$ are as previously defined and $L_6$ represents a bond or a $C_{1-5}$ alkylene chain optionally substituted by one or more $C_{1-4}$ alkyl groups, with a reducing agent, in an inert organic liquid at a temperature in the range from 0° C. up to the boiling point of the inert organic liquid to give compounds of formula I in which $R_7$ and $R_8$ represent hydrogen; or reacting a compound of formula X

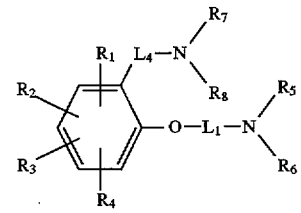

in which $R_1$, $R_2$, $R_3$, $R_4$, $R_5$, $R_6$, $R_7$, $R_8$ and $L_1$ are as previously defined and $L_4$ represents a group which on reduction gives $L_2$, with a reducing agent in an inert organic liquid at a temperature in the range from 0° C. up to the boiling point of the inert organic liquid; or g) reacting a compound of formula XI

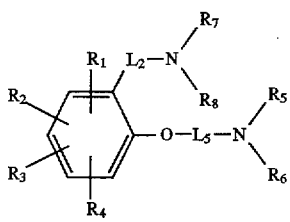

in which $R_1$, $R_2$, $R_3$, $R_4$, $R_5$, $R_6$, $R_7$, $R_8$ and $L_2$ are as previously defined and $L_5$ represents a group which on reduction gives $L_1$, with a reducing agent, in an inert organic liquid at a temperature in the range from 0° C. up to the boiling point of the inert organic liquid; or h) reacting a compound of formula XII

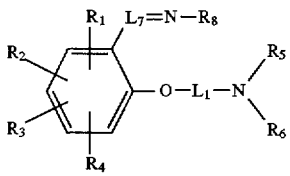

in which $R_1$, $R_2$, $R_3$, $R_4$, $R_5$, $R_6$ and $R_8$ are as previously defined and $L_7=N-R_8$ represents a group which on reduction gives $L_2-NHR_8$, with a reducing agent in an inert organic liquid at a temperature in the range from 0° C. up to the boiling point of the inert organic liquid to give compounds of formula I in which $R_7$ represents hydrogen; or i) by reacting a compound of formula XIII

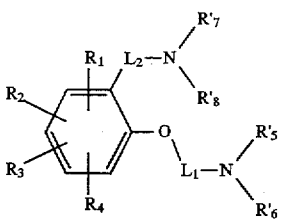

in which at least one of $R'_5$, $R'_6$, $R'_7$ and $R'_8$ represents a group which on reduction gives $R_5$, $R_6$, $R_7$ and $R_8$ respectively, and the remainder (if any) represent $R_5$, $R_6$, $R_7$ and $R_8$ respectively, with a reducing agent, in an inert organic liquid at a temperature in the range from 0° C. up to the boiling point of the inert organic liquid; or j) by reacting a compound of formula XIV

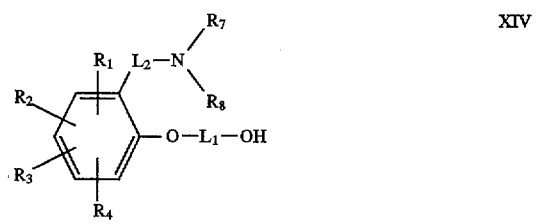

in which $R_1$, $R_2$, $R_3$, $R_4$, $R_7$, $R_8$, $L_1$ and $L_2$ are as previously defined, with a compound of formula XXV $$HNR_5R_6 \qquad XXV$$

in which $R_5$ and $R_6$ are as previously defined, in the presence of a dialkyl azodicarboxylate and a phosphorus (III) reagent, in the presence of an inert organic liquid at a temperature in the range of from 0° C. up to the boiling point of the inert organic liquid; or k) reacting a compound of formula XXVI

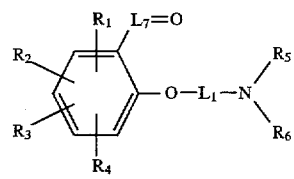

in which $R_1$, $R_2$, $R_3$, $R_4$, $R_5$, $R_6$ and $L_1$ are as previously defined and $L_7$ represents a group which on reduction gives $L_2$, with 1) an amine of formula $R_7R_8NH$, in the presence of an inert organic liquid at a temperature in the range from 0° C. up to the boiling point of the inert organic liquid, and then with
2) a reducing agent in the presence of an inert organic liquid at a temperature in the range from 0° C. up to the boiling point of the inert organic liquid; or l) alkylating a compound of formula I in which at least one of $R_5$, $R_6$, $R_7$ or $R_8$, respectively, represents hydrogen, using an alkylating agent of formula $R_5X$, $R_6X$, $R_7X$ or $R_8X$, respectively, in which X represents a leaving group, in the presence of an organic liquid at a temperature in the range 0°–150° C., to give compounds of formula I in which at least one of $R_5$, $R_6$, $R_7$ or $R_8$ represents a group other than hydrogen; or m) reductive alkylation of a compound of formula I in which at least one of $R_5$, $R_6$, $R_7$ and $R_8$, respectively, represents hydrogen comprising reaction with an aldehyde or a ketone, in the presence of a reducing agent, optionally in the presence of an inert organic liquid, at a temperature in the range 0°–250° C., to give a compound of formula I in which at least one $R_5$, $R_6$, $R_7$ or $R_8$ respectively, represents a group other than hydrogen.

* * * * *

UNITED STATES PATENT AND TRADEMARK OFFICE
CERTIFICATE OF CORRECTION

PATENT NO. : 5,736,568
DATED : April 7, 1998
INVENTOR(S) : RAFFERTY et al.

It is certified that error appears in the above-identified patent and that said Letters Patent is hereby corrected as shown below:

Column 44, claim 12, line 51, insert --(f) -- before "reacting".

Signed and Sealed this

Ninth Day of June, 1998

Attest:

BRUCE LEHMAN

Attesting Officer        Commissioner of Patents and Trademarks